US012650436B2

(12) United States Patent
Chan et al.

(10) Patent No.: US 12,650,436 B2
(45) Date of Patent: \*Jun. 9, 2026

(54) DETECTION OF VITAMINS A AND E BY TANDEM MASS SPECTROMETRY

(71) Applicant: Quest Diagnostics Investments LLC, Secaucus, NJ (US)

(72) Inventors: Sum Chan, San Clemente, CA (US); Qibo Jiang, Los Angeles, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/444,100

(22) Filed: Jan. 8, 2026

(65) Prior Publication Data

US 2026/0140125 A1      May 21, 2026

Related U.S. Application Data

(63) Continuation of application No. 18/940,701, filed on Nov. 7, 2024, which is a continuation of application No. 18/070,143, filed on Nov. 28, 2022, now Pat. No. 12,174,203, which is a continuation of application No. 17/114,276, filed on Dec. 7, 2020, now Pat. No. 11,513,130, which is a continuation of application No. 16/270,997, filed on Feb. 8, 2019, now Pat. No. 10,859,584, which is a continuation of application No. 13/231,866, filed on Sep. 13, 2011, now Pat. No. 10,215,765.

(60) Provisional application No. 61/383,280, filed on Sep. 15, 2010.

(51) Int. Cl.
| | |
|---|---|
| *G01N 33/82* | (2006.01) |
| *G01N 33/48* | (2006.01) |
| *H01J 49/00* | (2006.01) |
| *H01J 49/26* | (2006.01) |

(52) U.S. Cl.
CPC ............ *G01N 33/82* (2013.01); *G01N 33/48* (2013.01); *G01N 2560/00* (2013.01); *H01J 49/0045* (2013.01); *Y10T 436/24* (2015.01)

(58) Field of Classification Search
CPC .... G01N 2560/00; G01N 33/48; G01N 33/49; G01N 33/82; G01N 30/7233; H01J 49/004; H01J 49/0045; Y10T 436/142222; Y10T 436/200833; Y10T 436/203332; Y10T 436/24; A61K 31/355; A61K 31/07
USPC ..... 436/63, 93, 128, 131, 161, 173; 250/282
See application file for complete search history.

(56) References Cited

U.S. PATENT DOCUMENTS

| | | | | |
|---|---|---|---|---|
| 5,772,874 | A | 6/1998 | Quinn et al. | |
| 5,795,469 | A | 8/1998 | Quinn et al. | |
| 5,919,368 | A | 7/1999 | Quinn et al. | |
| 5,968,367 | A | 10/1999 | Quinn et al. | |
| 6,107,623 | A | 8/2000 | Bateman et al. | |
| 6,124,137 | A | 9/2000 | Hutchens et al. | |
| 6,204,500 | B1 | 3/2001 | Whitehouse et al. | |
| 6,268,144 | B1 | 7/2001 | Koester | |
| 10,215,765 | B2 * | 2/2019 | Chan | G01N 33/82 |
| 10,859,584 | B2 * | 12/2020 | Chan | G01N 33/82 |
| 10,859,585 | B2 | 12/2020 | Cravatt et al. | |
| 11,513,130 | B2 * | 11/2022 | Chan | G01N 33/82 |
| 12,174,203 | B2 * | 12/2024 | Chan | G01N 33/82 |
| 2008/0311671 | A1 | 12/2008 | Jiang et al. | |
| 2010/0155592 | A1 * | 6/2010 | Yang | G01N 33/82 |
| | | | | 250/282 |
| 2012/0164741 | A1 | 6/2012 | Chen et al. | |
| 2013/0306853 | A1 * | 11/2013 | Eastwood | G01N 33/743 |
| | | | | 250/288 |
| 2013/0316926 | A1 | 11/2013 | Caffrey | |
| 2022/0187304 | A1 * | 6/2022 | Rehnmark | G01N 33/942 |
| 2022/0317137 | A1 * | 10/2022 | Zeng | G01N 33/82 |

FOREIGN PATENT DOCUMENTS

| | | | |
|---|---|---|---|
| WO | 03075006 A1 | 9/2003 | |
| WO | 2010041068 A1 | 4/2010 | |
| WO | 2010114897 A1 | 10/2010 | |

OTHER PUBLICATIONS

Andreoli et al. Analytical and Bioanalytical Chemistry, vol. 378, Nov. 4, 2003, pp. 987-994.*
Kelm et al. Lipids, vol. 36, No. 11, Nov. 2001, pp. 1277-1282.*
Nagy et al. Analytical Chemistry, vol. 79, No. 18, Sep. 15, 2007, pp. 7087-7096.*
Gundersen et al. Rapid Communications in Mass Spectrometry, vol. 21, 2007, pp. 1176-1186.*

(Continued)

*Primary Examiner* — Maureen Wallenhorst
(74) *Attorney, Agent, or Firm* — Quest Diagnostics, Inc.

(57) ABSTRACT

A method for determining a combined amount of β-tocopherol and γ-tocopherol in a sample by tandem mass spectrometry includes subjecting the sample to ionization under conditions suitable to produce one or more ions from the β-tocopherol and γ-tocopherol detectable by mass spectrometry; and determining the amount of one or more of the ions by tandem mass spectrometry. Tandem mass spectrometry methods of this disclosure involve fragmenting β-tocopherol and γ-tocopherol ions having a mass to charge ratio of about 416.35±0.80 into one or more fragment ions including a fragment ion having a mass to charge ratio of about 151.00±0.80, wherein the amount of the one or more ions determined is related to the combined amount of β-tocopherol and γ-tocopherol in the sample.

13 Claims, 14 Drawing Sheets

(56) References Cited

OTHER PUBLICATIONS

Advisory Action mailed Feb. 16, 2024 for U.S. Appl. No. 18/070,143, filed Nov. 28, 2022.

Andreoli R., et al., "Development of a Simplified Method for the Simultaneous Determination of Retinol, Alpha-Tocopherol, and Beta-Carotene in Serum by Liquid Chromatography-Tandem Mass Spectrometry with Atmospheric Pressure Chemical Ionization," Analytical and Bioanalytical Chemistry, 2004, vol. 378 (4), pp. 987-994.

Bartolucci G., et al., "Liquid Chromatography Tandem Mass Spectrometric Quantitation of Sulfamethazine and its Metabolites: Direct Analysis of Swine Urine by Triple Quadrupole and by Ion Trap Mass Spectrometry," Rapid Communications in Mass Spectrometry, 2000, vol. 14 (11), pp. 967-973.

Budde P., et al., "Peptidomics Biomarker Discovery in Mouse Models of Obesity and Type 2 Diabetes," Combinatorial Chemistry and High Throughput Screening, 2005, vol. 8 (8), pp. 775-781.

Cabaleiro D.R., et al., "Feasibility of Standardization of Serum C-peptide Immunoassays with Isotope-dilution Liquid Chromatography-tandem Mass Spectrometry ," Clinical Chemistry, 2006, vol. 52 (6), pp. 1193-1196.

Capote P. F., et al., "Identification and Determination of Fat-Soluble Vitamins and Metabolites in Human Serum by Liquid Chromatography/ Triple Quadrupole Mass Spectrometry with Multiple Reaction Monitoring," Rapid Communications in Mass Spectrometry, 2007, vol. 21 (11), pp. 1745-1754.

Dueker S.R., et al., "Stable Isotope Methods for the Study of Beta Carotene—d8 Metabolism in humans Utilizing Tandem Mass Spectrometry and High-Performance Liquid Chromatography," Analytical Chemistry, 1994, vol. 66 (23), pp. 4177-4185.

Extended European Search Report for Application No. 21170624.7, mailed on Jul. 8, 2021, 14 pages.

Fierens C., et al., "Application of a C-peptide Electrospray Ionization-isotope Dilution-liquid Chromatography-tandem Mass Spectrometry Measurement Procedure for the Evaluation of Five C-peptide Immunoassays for Urine.," Journal of Chromatography B: Biomedical Sciences and Applications, 2003, vol. 792 (2), pp. 249-259.

Fierens C., et al., "Matrix Effect in the Quantitative Analysis of Urinary C-peptide by Liquid Chromatography/mass Spectrometry," Rapid Communications in Mass Spectrometry, 2000, vol. 14 (10), pp. 936-937.

Fierens C., et al., "Quantitative Analysis of Urinary C-peptide by Liquid Chromatography-tandem Mass Spectrometry with a Stable Isotopically Labelled Internal Standard," Journal of Chromatography, 2000, vol. 896 (1-2), pp. 275-278.

Final Office Action mailed Nov. 20, 2023 for U.S. Appl. No. 18/070,143, filed Nov. 28, 2022.

Final Office Action mailed Jan. 22, 2016 for U.S. Appl. No. 13/231,866, filed Sep. 13, 2011.

Final Office Action mailed Oct. 29, 2019 for U.S. Appl. No. 16/270,997, filed Feb. 8, 2019.

Gundersen T.E., et al., "Quantitative High-throughput Determination of Endogenous Retinoids in Human Plasma Using Triple-Stage Liquid Chromatography/Tandem Mass Spectrometry," Rapid Communications in Mass Spectrometry, Feb. 2007, vol. 21, pp. 1176-1186.

Hao Z., et al., "Simultaneous Quantification of Alpha-Tocopherol and Four Major Carotenoids in Botanical Materials by Normal Phase Liquid Chromatography-Atmospheric Pressure Chemical Ionization-Tandem Mass Spectrometry," Journal of Chromatography A, 2005, vol. 1094 (1-2), pp. 83-90.

Heudi O., et al., "Simultaneous Quantification of Vitamins A, D3 and E in Fortified Infant Formulae by Liquid Chromatography-Mass Spectrometry," Journal of Chromatography, 2004, vol. 1022 (1-2), pp. 115-123.

Kamao M., et al., "C-3 Epimerization of Vitamin D3 Metabolites and Further Metabolism of C-3 Epimers," The Journal of Biological Chemistry, 2004, vol. 279 (16), pp. 15897-15907.

Kamao M., et al., "Quantification of Fat-Soluble Vitamins in Human Breast Milk by Liquid Chromatography-tandem Mass Spectrometry," Journal of Chromatography B, 2007, vol. 859 (2), pp. 192-200.

Keltner Z., et al., "Mass Spectrometric Characterization and Activity of Zinc-activated Proinsulin C-peptide and C-peptide Mutants," The Analyst, 2010, vol. 135 (2), pp. 278-288.

Khachik F., et al., "Separation and Identification of Carotenoids and their Oxidation Products in the Extracts of Human Plasma," Analytical Chemistry, 1992, vol. 64 (18), pp. 2111-2122.

Khachik F., et al., "Identification, Quantification, and Relative Concentrations of Carotenoids and their Metabolites in Human Milk and Serum," Analytical Chemistry, 1997, vol. 69 (10), pp. 1873-1881.

Lauridsen C., et al., "Quantitative Analysis by Liquid Chromatography-Tandem Mass Spectrometry of Deuterium-Labeled and Unlabeled Vitamin E in Biological Samples," Analytical Biochemistry, 2001, vol. 289, pp. 89-95.

Li H., et al., "Determination of Carotenoids and All-Trans-Retinol in Fish Eggs by Liquid Chromatography-Electrospray Ionization-Tandem Mass Spectrometry," Journal of Chromatography B, 2005, vol. 816 (1-2), pp. 49-56.

Merchant M., et al., "Recent Advancements in Surface-Enhanced Laser Desorption/Ionization-Time of Flight-Mass Spectrometry," Electrophoresis, 2000, vol. 21 (6), pp. 1164-1167.

Mottier P., et al., "Comparison of Gas Chromatography-Mass Spectrometry and Liquid Chromatographytandem Mass Spectrometry Methods to Quantify Alpha-Tocopherol and Alpha-Tocopherolquinone Levels in Human Plasma," Analytical Biochemistry, 2002, vol. 301 (1), pp. 128-135.

Nagy K., et al., "Comprehensive Analysis of Vitamin E Constituents in Human Plasma by Liquid Chromatography-Mass Spectrometry," Analytical Chemistry, 2007, vol. 79 (18), pp. 7087-7096.

Non-Final Office Action mailed Jun. 1, 2015 for U.S. Appl. No. 13/231,866, filed Sep. 13, 2011.

Non-Final Office Action mailed Apr. 5, 2022 for U.S. Appl. No. 17/114,276, filed Dec. 7, 2020.

Non-Final Office Action mailed Oct. 9, 2014 for U.S. Appl. No. 13/231,866, filed Sep. 13, 2011.

Non-Final Office Action mailed Mar. 15, 2024 for U.S. Appl. No. 18/070,143, filed Nov. 28, 2022.

Non-Final Office Action mailed Jan. 22, 2016 for U.S. Appl. No. 14/063,956, filed Oct. 25, 2013.

Non-Final Office Action mailed Mar. 25, 2019 for U.S. Appl. No. 16/270,997, filed Feb. 8, 2019.

Patent Board Decision mailed Aug. 24, 2018 for U.S. Appl. No. 13/231,866, filed Sep. 13, 2011.

Polson C., et al., "Optimization of Protein Precipitation Based Upon Effectiveness of Protein Removal and Ionization Effect in Liquid Chromatography-Tandem Mass Spectrometry," Journal of Chromatography B, 2003, vol. 785 (2), pp. 263-275.

Robb D.B., et al., "Atmospheric Pressure Photoionization: An Ionization Method for Liquid Chromatography-Mass Spectrometry," Analytical Chemistry, 2000, vol. 72 (15), pp. 3653-3659.

Rogatsky E., et al., "Sensitive Quantitative Analysis of C-Peptide Human Plasma by 2-Dimensional Liquid Chromatography-Mass Spectrometry Isotope-Dilution Assay," Clinical Chemistry, May 2006, vol. 52 (5), pp. 872-879.

Ruhl R., "Method to Determine 4-Oxo-Retinoic Acids, Retinoic Acids and Retinol in Serum and Cell Extracts By Liquid Chromatography/Diode-Array Detection Atmospheric Pressure Chemical Ionization Tandem Mass Spectrometry," Rapid Communications in Mass Spectrometry, 2006, vol. 20 (16), pp. 2497-2504.

Stoggl W., et al., "Simultaneous Determination of Carotenoids, Tocopherols, and Gamma-Oryzanol in Crude Rice Bran Oil by Liquid Chromatography Coupled to Diode Array and Mass Spectrometric Detection Employing Silica C30 Stationary Phases," Journal of Separation Science, 2005, vol. 28 (14), pp. 1712-1718.

Tang X.H., et al., "Cell Proliferation Inhibition and Alterations in Retinol Esterification Induced by Phytanic Acid and Docosahexaenoic Acid," The Journal of Lipid Research, 2007, vol. 48 (1), pp. 165-176.

(56) References Cited

OTHER PUBLICATIONS

U.S. Appl. No. 18/070,143, Non-Final Office Action dated Jul. 12, 2023.

Walton T.J., et al., "Tandem Mass Spectrometry in Vitamin E Anaylsis," Biomedical & environmental mass spectrometry, 1988, vol. 16 (1-12), pp. 289-298.

Wang Y., et al., "Simultaneous Determination Of All-Trans, 9-Cis, 13-Cis Retinoic Acid And Retinol In Rat Prostate Using Liquid Chromatography-Mass Spectrometry," Journal of Mass Spectrometry, 2001, vol. 36 (8), pp. 882-888.

Wright Jr., G.L., et al., "Proteinchip Surface Enhanced Laser Desorption/Ionization (SELDI) Mass Spectrometry: A Novel Protein Biochip Technology for Detection of Prostate Cancer Biomarkers in Complex Protein Mixtures," Prostate Cancer and Prostatic Diseases, 1999, vol. 2 (5-6), pp. 264-276.

Zimmer D., et al., "Comparison of Turbulent-Flow Chromatography with Automated Solid-Phase Extraction in 96-Well Plates and Liquid-Liquid Extraction Used As Plasma Sample Preparation Techniques for Liquid Chromatography-Tandem Mass Spectrometry," Journal of Chromatography A, 1999, vol. 854, pp. 23-35.

* cited by examiner

FULL: PRO: 439  CE: -35  CT: 0.55

DETECTION OF VITAMINS A AND E BY TANDEM MASS SPECTROMETRY

CROSS-REFERENCED TO RELATED APPLICATIONS

This application is a continuation of U.S. application Ser. No. 18/940,701, filed Nov. 7, 2024, which is a continuation of U.S. patent application Ser. No. 18/070,143, filed on Nov. 28, 2022, now U.S. Pat. No. 12,174,203, which is a continuation of U.S. patent application Ser. No. 17/114,276, filed on Dec. 7, 2020, now U.S. Pat. No. 11,513,130, which is a continuation of U.S. patent application Ser. No. 16/270, 997, filed on Feb. 8, 2019, now U.S. Pat. No. 10,859,584, which is a continuation of U.S. patent application Ser. No. 13/231,866, filed on Sep. 13, 2011, now U.S. Pat. No. 10,215,765, which claims the benefit of priority to U.S. Provisional Patent Application No. 61/383,280, filed Sep. 15, 2010, all of which are incorporated by reference herein in their entirety.

FIELD OF THE INVENTION

The invention relates to the quantitative measurement of one or more of vitamin A (retinol), α-tocopherol, and β-tocopherol and/or γ-tocopherol. In a particular aspect, the invention relates to methods for quantitative measurement of one or more of these vitamins by mass spectrometry.

BACKGROUND OF THE INVENTION

The following description of the background of the invention is provided simply as an aid in understanding the invention and is not admitted to describe or constitute prior art to the invention.

There are five major fat-soluble vitamins or vitamin related substances in humans: vitamins A, K, D, and E, and carotene. Vitamin A (retinol) is the immediate precursor of two important biologically active metabolites: retinal (needed for scotopic and color vision), and retinoic acid (a hormone-like growth factor for epithelial and other cells). Thus retinol is associated with the function of vision, epithelial cell integrity, bone remodeling, and reproduction. Vitamin E exists in eight different forms (isomers): alpha (α), beta (β), gamma (γ), and delta (δ)-tocopherol; and alpha (α), beta (β), gamma (γ), and delta (δ) tocotrienol. Alpha-tocopherol is the most active form of vitamin E in humans, and may be an important lipid-soluble antioxidant in the protection of cell membranes from oxidation from radicals produced in the oxidation of fats. Alpha-tocopherol is the most studied of the vitamin E isomers, with all other forms much less studied.

Various methods have been reported in the art for measuring vitamin A, α-tocopherol, β-tocopherol and γ-tocopherol, either individually or in various combinations. For reports of detection of vitamin A, see e.g., Deuker, S., et al., *Anal. Chem.* 1994, 66:4177-85 (reporting quantitation of derivatized retinol by gas chromatography-mass spectrometry); Wang, Y., et al., *J. Mass Spectrom.* 2001, 36:882-88 (reporting quantitation of vitamin A (retinol) in rat prostate with liquid chromatography-mass spectrometry); Li H., et al., et al., *J. Chromatog. B* 2005, 816:49-56 (reporting quantitation of all-trans-retinol in fish eggs by liquid chromatography-tandem mass spectrometry with positive electrospray ionization); Rühl, R., *Rapid Commun. Mass Spectrom.* 2006, 20:2497-2504 (reporting quantitation of retinol in serum and cell extracts by liquid chromatography-diodearray detection atmospheric pressure chemical ionization tandem mass spectrometry). For reports of detection of α-tocopherol and/or γ-tocopherol, see e.g., Walton, T., et al., *Biomed. Environ Mass Spectrom.* 1988, 16:289-98 (reporting fragmentation spectra of α and γ forms of tocopherol generated by tandem mass spectrometry of pure samples); Lauridsen, C., et al., *Anal. Biochem.* 2001, 289:89-95 (reporting quantitation of α-tocopherol in plasma by HPLC-tandem mass spectrometry); Mottier, P., et al., *Anal. Biochem.* 2002, 301:128-135 (reporting quantitation of α-tocopherol in plasma by GC-tandem mass spectrometry and HPLC-tandem mass spectrometry); Hao, Z., et al., *J. Chromatog. A* 2005, 1094:83-90 (reporting quantitation of α-tocopherol in botanical materials by liquid chromatography-tandem mass spectrometry); Stöggl, W., et al., J. Sep. Sci. 2005, 28:1712-18 (reporting reverse phase liquid chromatographic separation of α-tocopherol and γ-tocopherol with a C-30 chromatography column); and Nagy, K., et al., *Anal. Chem.* 2007, 79:7087-96 (reporting quantitation α-tocopherol and γ-tocopherol in plasma with normal phase liquid chromatography-tandem mass spectrometry). For reports of detection of two or more of vitamin A, α-tocopherol, and γ-tocopherol, see e.g., Khachik, F., et al., *Anal. Chem.* 1992, 64:2111-22 (reporting detection of vitamin A, α-tocopherol, and γ-tocopherol from extracts of human plasma with HPLC); Khachik, F., et al., *Anal. Chem.* 1997, 69:1873-81 (reporting quantitation of vitamin A, α-tocopherol, and γ-tocopherol in serum and breast milk with high performance liquid chromatography-photodiode array detection-mass spectrometry); Heudi, O., et al., *J. Chromatog. A* 2004, 1022:115-23 (reporting simultaneous quantitation of vitamin A and E (form unspecified) in infant formulae by liquid chromatography-mass spectrometry); Andreoli, R., et al., *Anal. Bioanal. Chem.* 2004, 378:987-94 (reporting simultaneous determination of vitamins A (retinol) and α-tocopherol in serum with liquid chromatography-tandem mass spectrometry); Capote, F., et al., *Rapid Commun. Mass Spectrom.* 2007, 21:1745-54 (reporting quatitation of liposoluble vitamins including vitamin A (all-trans-retinol) and α-tocopherol in human serum with liquid chromatography-triple quadrupole tandem mass spectrometry); and Kamao, M., et al., *J. Chromatog. B* 2004, 1022:115-23 (reporting quantitation of fat soluble vitamins (including vitamins A (retinol) and α-tocopherol) in breast milk by liquid chromatography-tandem mass spectrometry).

SUMMARY OF THE INVENTION

The present invention provides methods for detecting the presence or amount of one or more of vitamin A, α-tocopherol, and the combined amount of β-tocopherol and γ-tocopherol in a sample by tandem mass spectrometry. The methods include subjecting the sample to ionization under conditions suitable to produce one or more ions detectable by mass spectrometry; determining the amount of said one or more ions by tandem mass spectrometry; and using the amount of the one or more ions to determine the amount of one or more of vitamin A, α-tocopherol, and the combined amount of β-tocopherol and γ-tocopherol in the sample.

In one aspect, the present invention provides methods for determining the amount of vitamin A in a sample by tandem mass spectrometry. These methods include subjecting vitamin A from the sample to ionization under conditions suitable to produce one or more ions detectable by mass spectrometry; determining the amount of one or more of the ions by tandem mass spectrometry; and using the determined amounts of the one or more ions to determine the amount of vitamin A in the sample. In these embodiments, tandem mass spectrometry includes fragmenting a vitamin A precursor ion with a mass to charge ratio of about 269.30±0.80 into one or more fragment ions comprising a fragment ion with mass to charge ratio of about 105.00±0.80. In some embodiments, the ion masses for the vitamin A precursor and fragment ions are those indicated ±0.50.

In some related embodiments, the sample is subjected to liquid chromatography (LC) (such as reverse phase LC) prior to ionization. In some related embodiments, the LC is HPLC. In some related embodiments, the LC and ionization are conducted with on-line processing.

In some related embodiments, the methods are also used to simultaneously determine the amount of one or more analytes in addition to vitamin A. In some related embodiments, these additional analytes include one or both of α-tocopherol and combined β-tocopherol and γ-tocopherol. In some embodiments, the additional analytes include α-tocopherol and combined β-tocopherol and γ-tocopherol.

In some methods where α-tocopherol is determined by tandem mass spectrometry, determining the amount of α-tocopherol includes fragmenting a α-tocopherol precursor ion with a mass to charge ratio of about 430.47±0.80 into one or more fragment ions comprising a fragment ion with mass to charge ratio of about 165.03±0.80. In some embodiments, the ion masses for the α-tocopherol precursor and fragment ions are those indicated ±0.50.

In some embodiments where the combined amount of β-tocopherol and γ-tocopherol is determined by tandem mass spectrometry, determining the combined amount of β-tocopherol and γ-tocopherol comprises fragmenting β-tocopherol and/or γ-tocopherol precursor ions with a mass to charge ratio of about 416.35±0.80 into one or more fragment ions comprising a fragment ion with mass to charge ratio of about 151.00±0.80. In some embodiments, the ion masses for the β-tocopherol and/or γ-tocopherol precursor and fragment ions are those indicated±0.50.

In some embodiments, the sample comprises a biological sample; in related embodiments, the biological sample may be from a human patient suspected of having a deficiency or an excess of vitamin A. In some embodiments the sample comprises serum, such as human serum or plasma, such as EDTA plasma.

In embodiments utilizing tandem mass spectrometry, tandem mass spectrometry may be conducted by any method known in the art, including for example, multiple reaction monitoring, precursor ion scanning, or product ion scanning.

In embodiments which utilize two or more of an extraction column, an analytical column, and an ionization source, two or more of these components may be connected in an on-line fashion to allow for automated sample processing and analysis.

In certain preferred embodiments of the methods disclosed herein, mass spectrometry is performed in positive ion mode. Alternatively, mass spectrometry is performed in negative ion mode. Various ionization sources, including for example atmospheric pressure chemical ionization (APCI) or electrospray ionization (ESI), may be used in embodiments of the present invention. In certain preferred embodiments, one or more of vitamin A, α-tocopherol, and the combined β-tocopherol and γ-tocopherol are measured using APCI in positive ion mode.

In preferred embodiments, a separately detectable internal standard is provided in the sample, the amount of which is also determined in the sample. In these embodiments, all or a portion of both the analyte(s) of interest and the internal standard present in the sample are ionized to produce a plurality of ions detectable in a mass spectrometer, and one or more ions produced from each are detected by mass spectrometry. In these embodiments, the presence or amount of ions generated from the analyte(s) of interest may be related to the presence of amount of analyte of interest in the sample.

In other embodiments, the amount of one or more of vitamin A, α-tocopherol, and combined β-tocopherol and γ-tocopherol in a sample may be determined by comparison to one or more external reference standards. Exemplary external reference standards include blank plasma or serum spiked with one or more of vitamin A, α-tocopherol, β-tocopherol, and γ-tocopherol or isotopically labeled variants thereof.

As used herein, unless otherwise stated, the singular forms "a," "an," and "the" include plural reference. Thus, for example, a reference to "a protein" includes a plurality of protein molecules.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected precursor or fragment ions by mass spectrometry. Relative reduction as this term is used does not require that any substance, present with the analyte of interest in the material to be purified, is entirely removed by purification.

As used herein, the term "sample" refers to any sample that may contain an analyte of interest. As used herein, the term "body fluid" means any fluid that can be isolated from the body of an individual. For example, "body fluid" may include blood, plasma, serum, bile, saliva, urine, tears, perspiration, and the like. In preferred embodiments, the sample comprises a body fluid sample; preferably plasma or serum. In some embodiments, the body fluid is from a human patient, such as a human patient suspected of having a deficiency or an excess of one or more of vitamin A, α-tocopherol, and β-tocopherol and/or γ-tocopherol.

As used herein, the term "simultaneous" as applied to simultaneously ionizing and/or detecting the amount of two or more analytes from a sample means ionizing two or more analytes and/or acquiring data reflective of the amount of the two or more analytes in the sample from the same sample injection. The data for each analyte may be acquired sequentially or in parallel, depending on the instrumental techniques employed. For example, a single sample containing two analytes may be injected into an on-line HPLC column, which may then elute each analyte one after the other, resulting in introduction of the analytes into a mass spectrometer at two different times. Determining the amount of each of these two analytes is simultaneous for the purposes herein, as both analytes result from the same sample injection into the HPLC.

As used herein, the term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis. SPE, including TFLC, may operate via a unitary or mixed mode mechanism. Mixed mode mechanisms utilize ion exchange and hydrophobic retention in the same column; for example, the solid phase of a mixed-mode SPE column may exhibit strong anion exchange and hydrophobic retention; or may exhibit column exhibit strong cation exchange and hydrophobic retention.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), normal phase liquid chromatography (NPLC), high performance liquid chromatography (HPLC), and turbulent flow liquid chromatography (TFLC) (sometimes known as high turbulence liquid chromatography (HTLC) or high throughput liquid chromatography). As used herein, the term "reverse phase liquid chromatography" refers to any liquid chromatography technique in which the mobile phase is polar and the stationary phase is non-polar. As used herein, the term "normal phase liquid chromatography" refers to any liquid chromatography technique in which the mobile phase is non-polar and the stationary phase is polar.

As used herein, the term "high performance liquid chromatography" or "HPLC" (sometimes known as "high pressure liquid chromatography") refers to liquid chromatography in which the degree of separation is increased by forcing the mobile phase under pressure through a stationary phase, typically a densely packed column.

As used herein, the term "turbulent flow liquid chromatography" or "TFLC" (sometimes known as high turbulence liquid chromatography or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., *J Chromatogr A* 854: 23-35 (1999); see also, U.S. Pat. Nos. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 40 $\mu$m, such as greater than about 50 $\mu$m. As used in this context, the term "about" means$\pm$10%.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means$\pm$10%. In a preferred embodiment the analytical column contains particles of about 5 $\mu$m in diameter.

As used herein, the terms "on-line" and "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged species; and (2) detecting the molecular weight of the charged species and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 1999, 2: 264-76; and Merchant and Weinberger, *Electrophoresis* 2000, 21: 1164-67.

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the ionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See, e.g., Robb et al., *Anal. Chem.* 2000, 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase. Laser desorption thermal desorption is a technique wherein a sample containing the analyte is thermally desorbed into the gas phase by a laser pulse. The laser hits the back of a specially made 96-well plate with a metal base. The laser pulse heats the base and the heat causes the sample to transfer into the gas phase. The gas phase sample is then drawn into the mass spectrometer.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

As used herein, the term "lower limit of quantification", "lower limit of quantitation" or "LLOQ" refers to the point where measurements become quantitatively meaningful. The analyte response at this LOQ is identifiable, discrete and reproducible with a relative standard deviation (RSD %) of less than 20% and an accuracy of 85% to 115%.

As used herein, the term "limit of detection" or "LOD" is the point at which the measured value is larger than the uncertainty associated with it. The LOD is the point at which a value is beyond the uncertainty associated with its measurement and is defined as three times the RSD of the mean at the zero concentration.

As used herein, an "amount" of an analyte in a body fluid sample refers generally to an absolute value reflecting the mass of the analyte detectable in volume of sample. However, an amount also contemplates a relative amount in comparison to another analyte amount. For example, an amount of an analyte in a sample can be an amount which is greater than a control or normal level of the analyte normally present in the sample.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to ±0.80 atomic mass unit, such as ±0.50 atomic mass unit.

The summary of the invention described above is non-limiting and other features and advantages of the invention will be apparent from the following detailed description of the invention, and from the claims.

DETAILED DESCRIPTION OF THE INVENTION

Figure 1A:
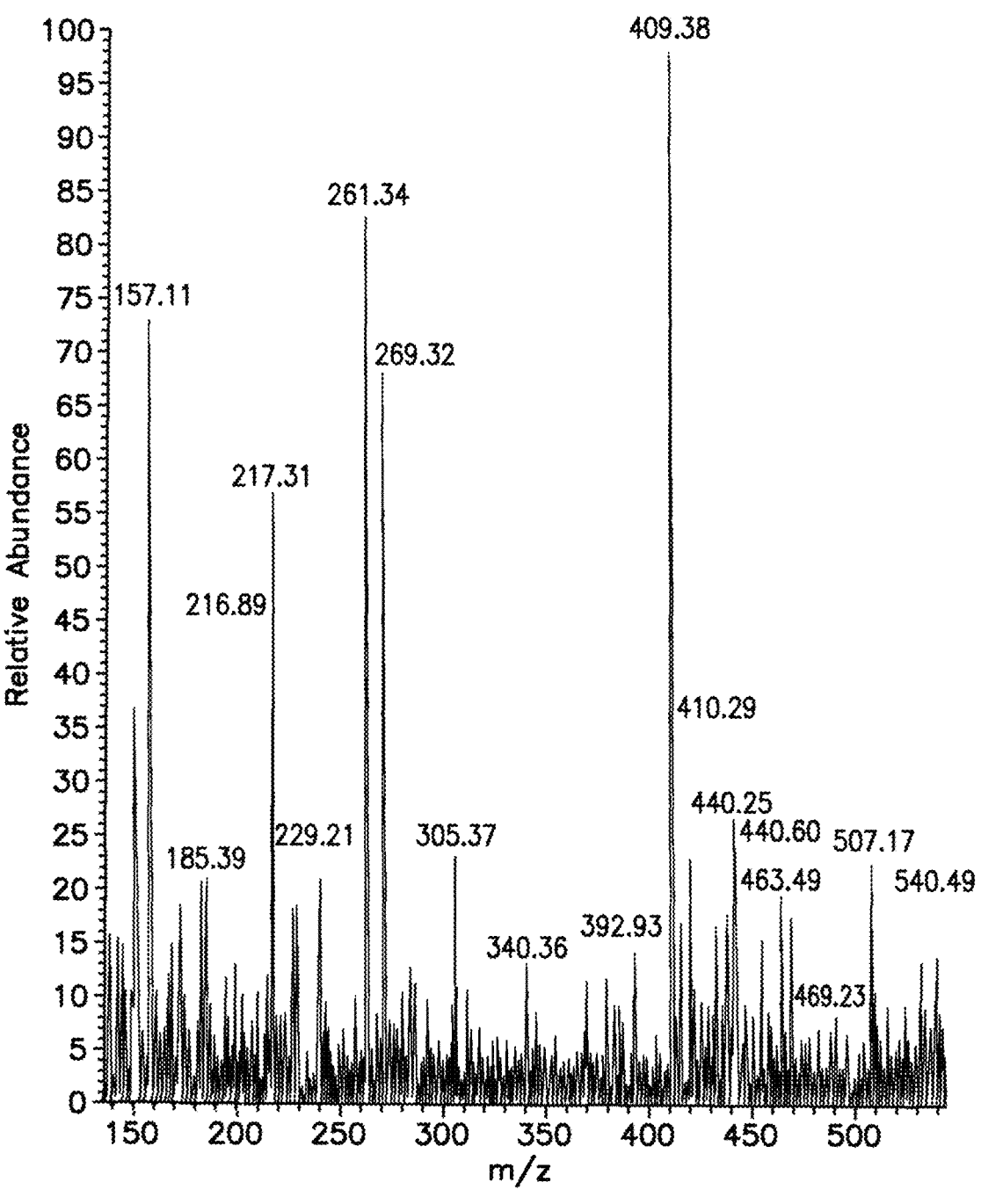
FIGS. 1A and B show exemplary precursor and fragmentation MS/MS spectra, respectively, for vitamin A. Details are discussed in Example 3.
Figure 1B:
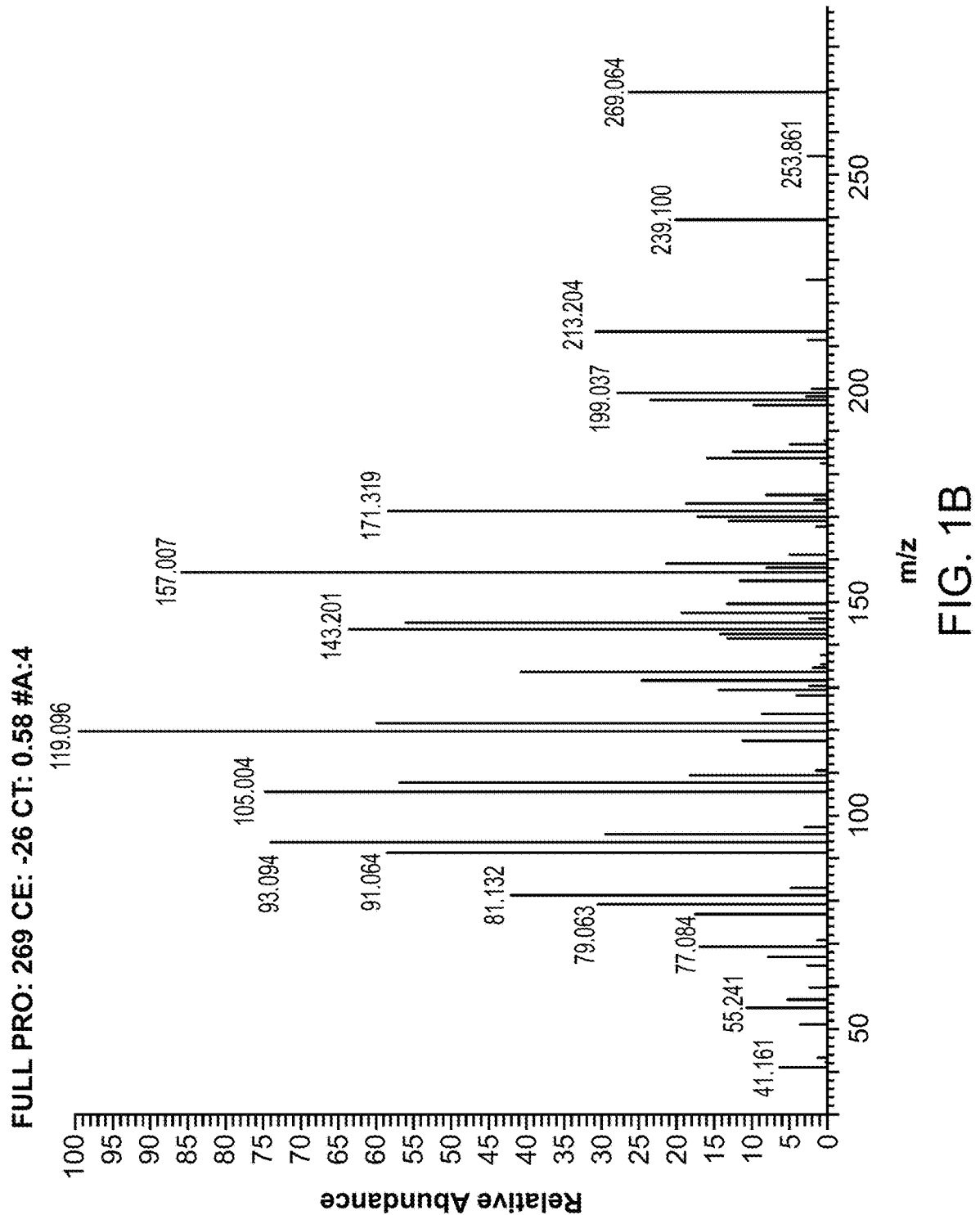
Figure 2A:
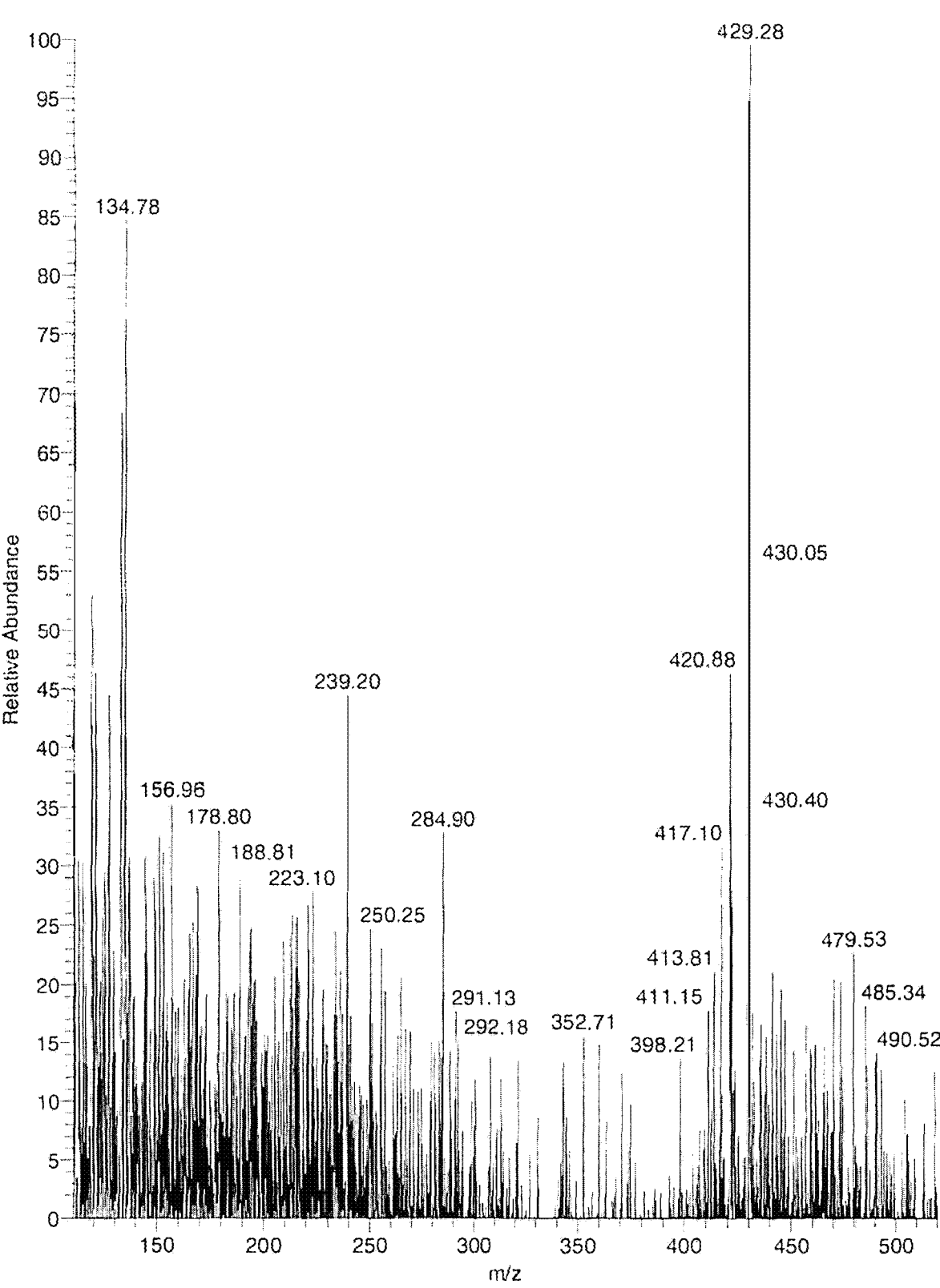
FIGS. 2A and B show exemplary precursor and fragmentation MS/MS spectra, respectively, for α-tocopherol. Details are discussed in Example 3.
Figure 2B:
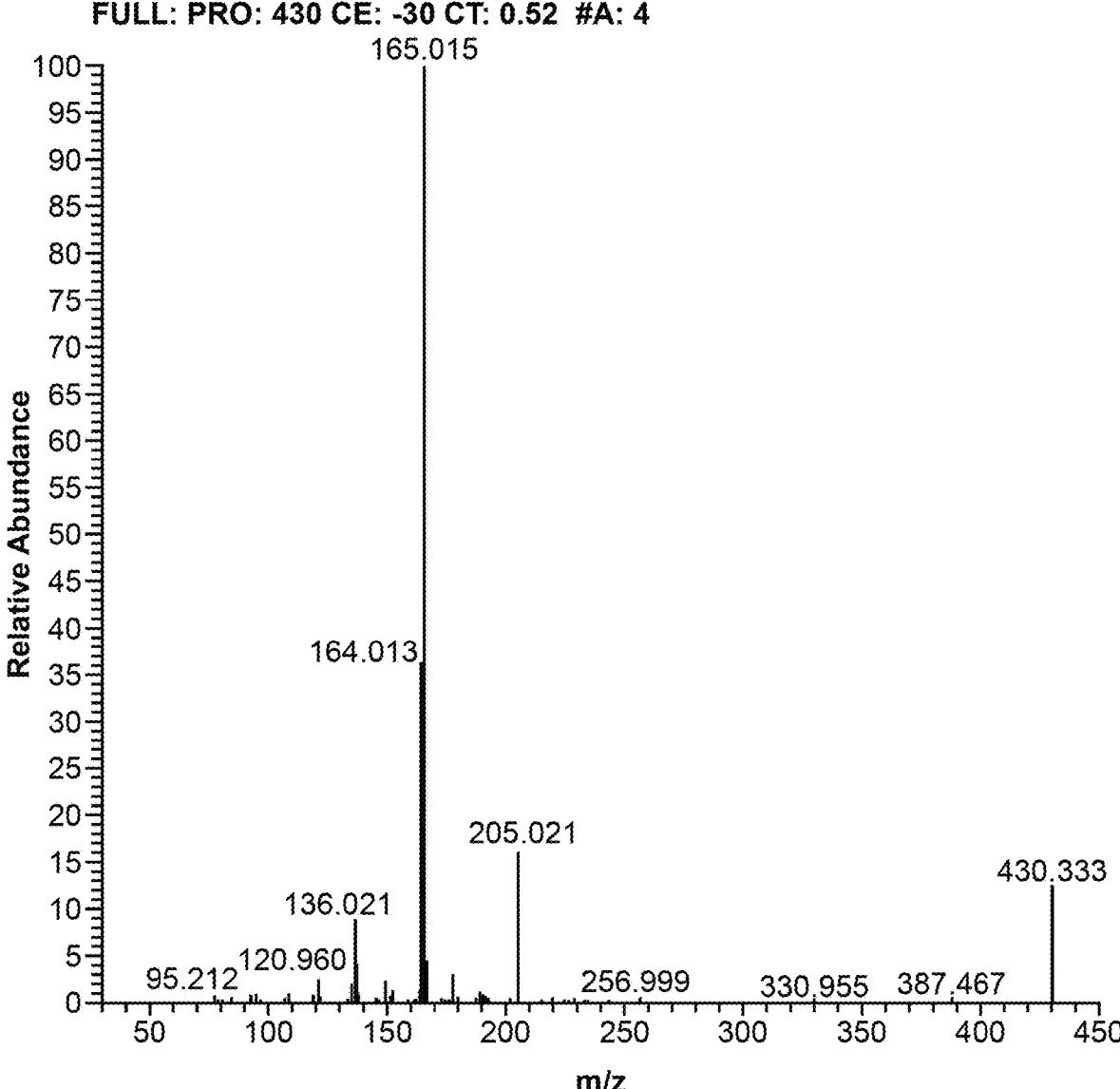
Figure 3A:
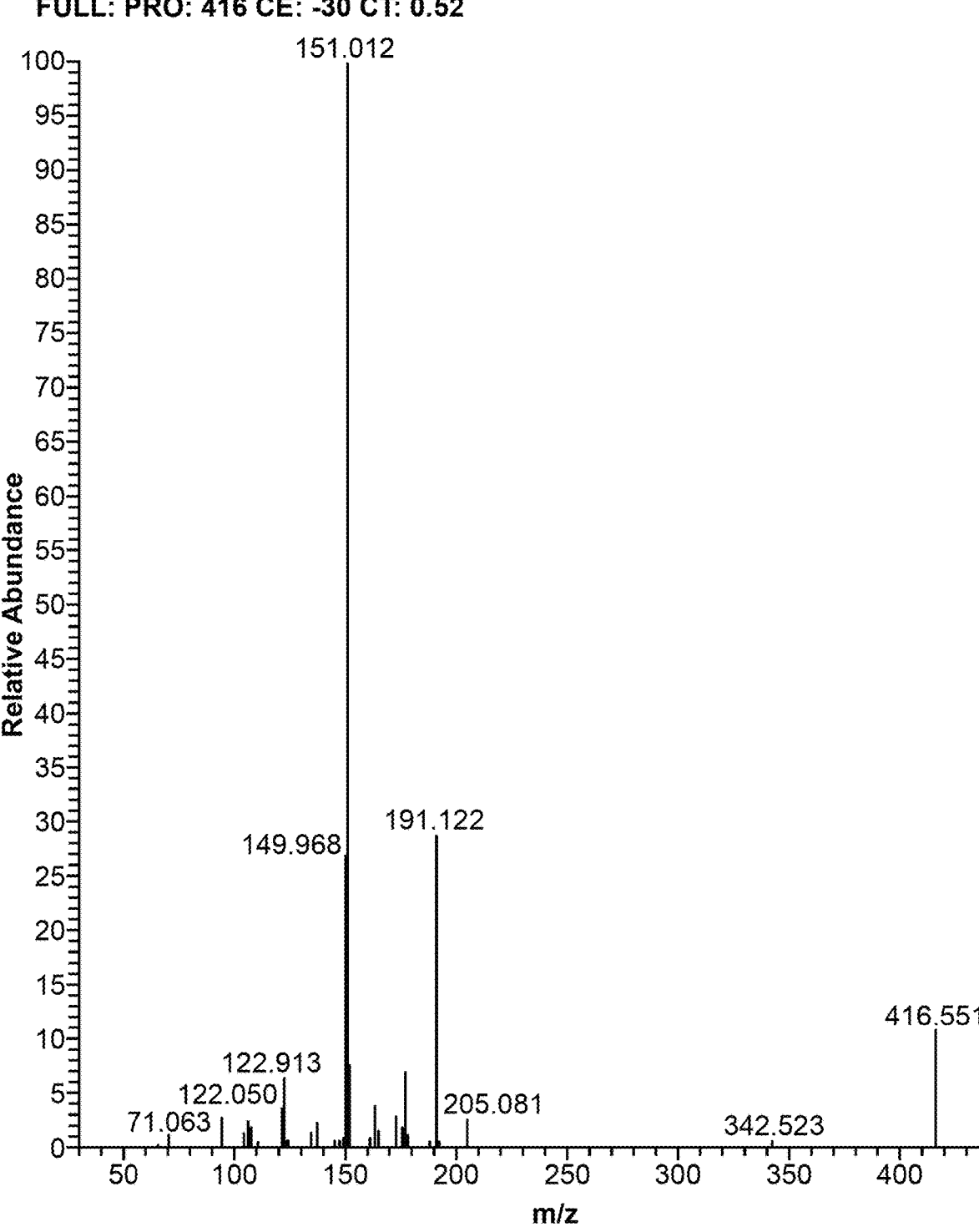
FIGS. 3A and B show exemplary precursor and fragmentation MS/MS spectra, respectively, for β-tocopherol and/or γ-tocopherol. Details are discussed in Example 3.
Figure 3B:
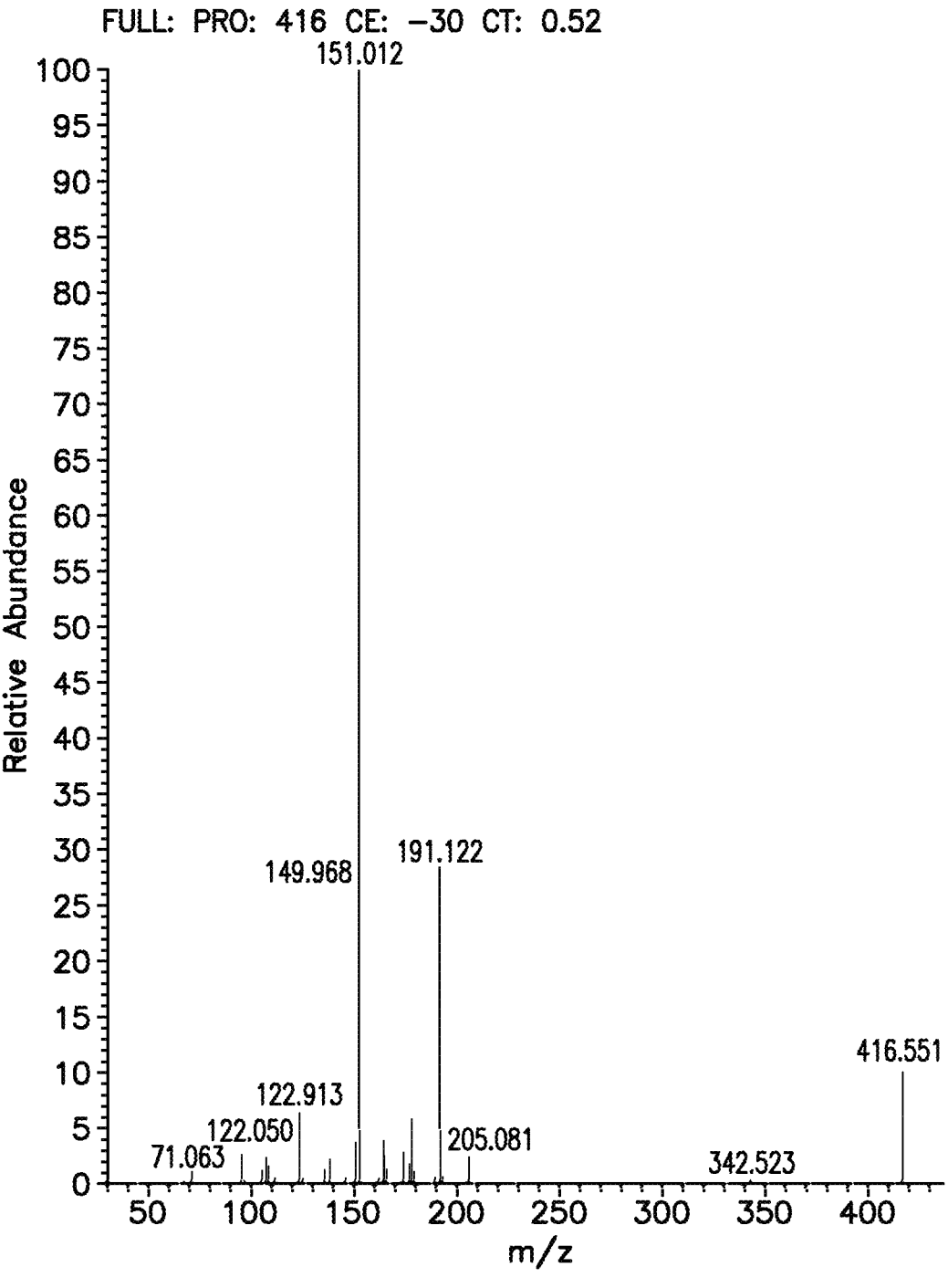
Figure 4A:
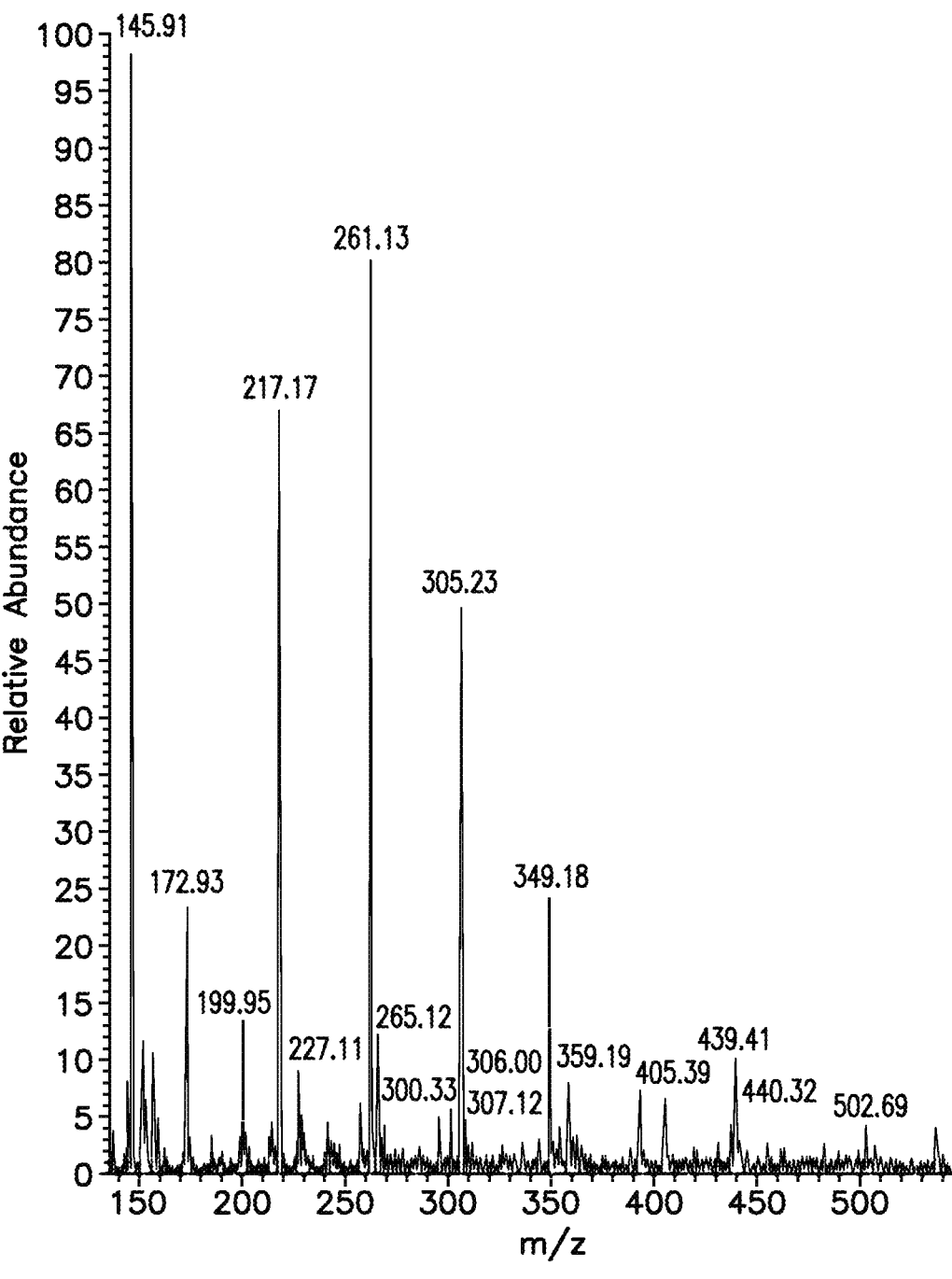
FIGS. 4A and B show exemplary precursor and fragmentation MS/MS spectra, respectively, for $d_9$-α-tocopherol. Details are discussed in Example 3.
Figure 4B:
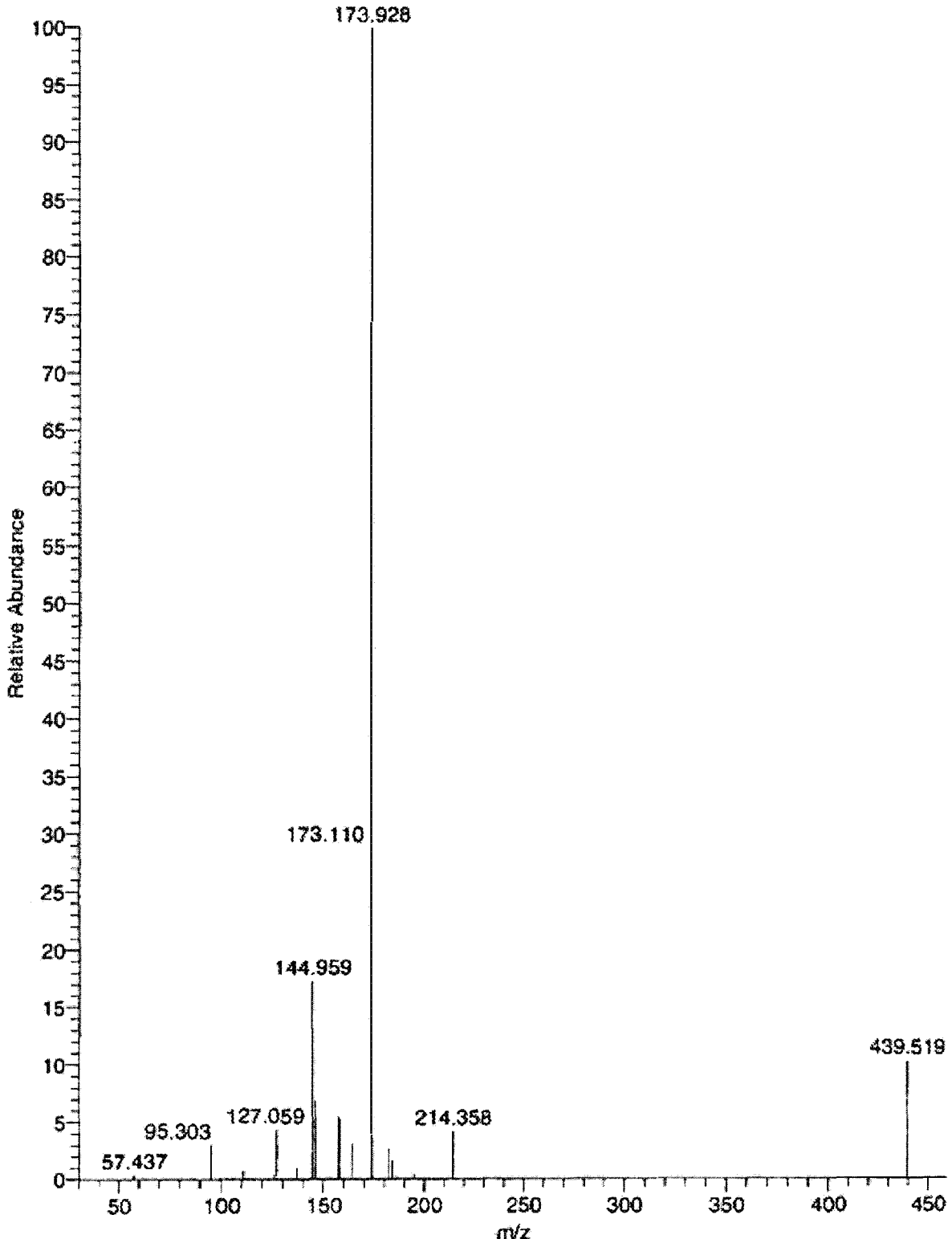
Figure 5:
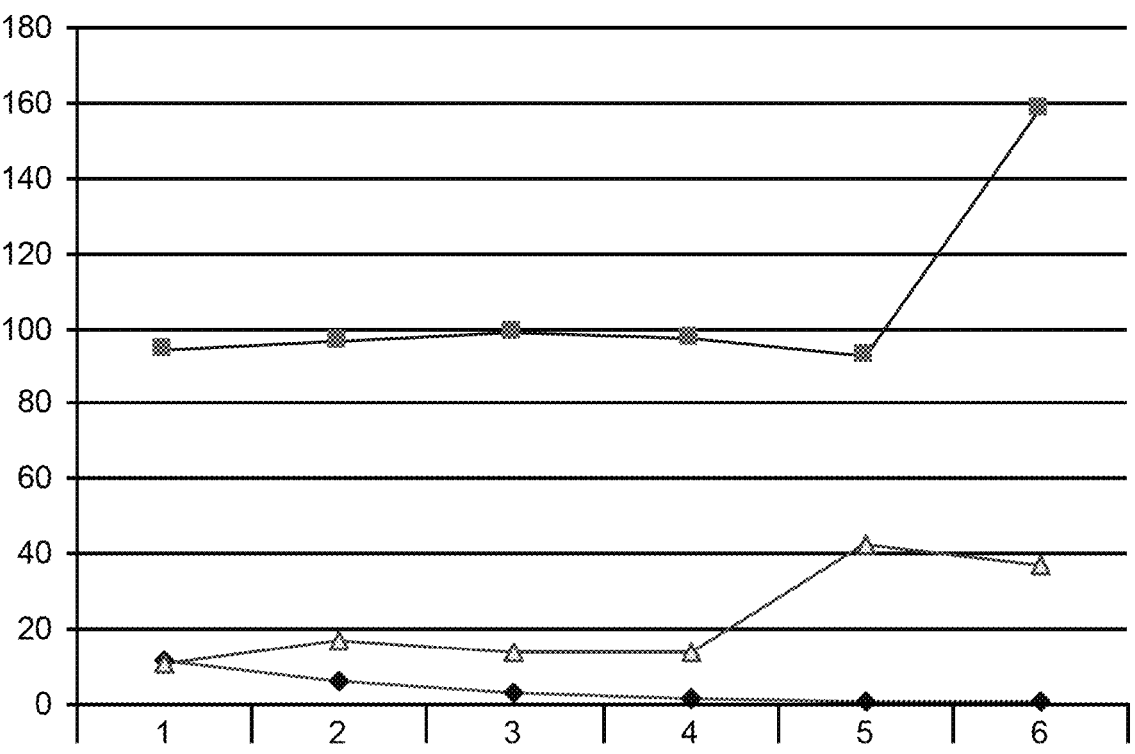
FIG. 5 shows a plot of the results from the lower linearity of quantitation studies for vitamin A. The data plotted with squares represent the accuracy (%); data plotted with triangles represent relative standard deviation (RSD %); and data plotted with diamonds represent concentration. Details are described in Example 4.

Methods are described for measuring the amount of one or more of vitamins A (retinol), α-tocopherol, and β-tocopherol and/or γ-tocopherol in a sample. More specifically, mass spectrometric methods are described for detecting and quantifying vitamin A, α-tocopherol, and β-tocopherol and/or γ-tocopherol in a sample. The methods may utilize liquid chromatography to perform a purification of selected analytes, combined with methods of mass spectrometry (MS), thereby providing a high-throughput assay system for detecting and quantifying the amount of one or more of vitamin A (retinol), α-tocopherol, and β-tocopherol and/or γ-tocopherol in a sample. The preferred embodiments are particularly well suited for application in large clinical laboratories for automated vitamin A (retinol), α-tocopherol, and β-tocopherol and γ-tocopherol quantification assay.

β-tocopherol and γ-tocopherol are positional isomers, each with a molar mass of about 416.88 a.m.u. In certain embodiments, ionization of β-tocopherol and γ-tocopherol under similar conditions will generate β-tocopherol and γ-tocopherol precursor ions with similar m/z. Further, tandem mass spectrometric methods which fragment similar β-tocopherol and γ-tocopherol precursor ions may result in generation of similar β-tocopherol and γ-tocopherol fragment ions. Thus in some embodiments, precursor and fragment ions from β-tocopherol may not be distinguished from precursor and fragment ions from γ-tocopherol. Thus, in some embodiments, the amount of particular precursor and fragment ions may correlate to the combined amount of β-tocopherol and/or γ-tocopherol in a sample.

Similarly, certain purification methods used in some of the methods described herein are unable to separate β-tocopherol and γ-tocopherol. For example, β-tocopherol and γ-tocopherol in a sample will co-elute when the sample is purified by certain liquid chromatography procedures. Thus, in some methods, β-tocopherol and γ-tocopherol will be introduced into the mass spectrometer at the same time if both β-tocopherol and γ-tocopherol are present in the sample.

Suitable test samples for use in methods of the present invention include any test sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Preferred samples comprise bodily fluids such as blood, plasma, serum, saliva, cerebrospinal fluid, or tissue samples; preferably plasma and serum. Such samples may be obtained, for example, from a patient; that is, a living person, male or female, presenting oneself in a clinical setting for diagnosis, prognosis, or treatment of a disease or condition. In embodiments where the sample comprises a biological sample, the methods may be used to determine the amount of one or more of vitamin A, α-tocopherol, and β-tocopherol and γ-tocopherol in the sample when the sample was obtained from the biological source (i.e., the amount of endogenous vitamin A, α-tocopherol, and β-tocopherol and γ-tocopherol in the sample).

The present invention also contemplates kits for a vitamin A, α-tocopherol, and β-tocopherol and γ-tocopherol quantitation assay. A kit for a vitamin A, α-tocopherol, and β-tocopherol and γ-tocopherol quantitation assay may include a kit comprising the compositions provided herein. For example, a kit may include packaging material and measured amounts of an isotopically labeled internal standard, in amounts sufficient for at least one assay. Typically, the kits will also include instructions recorded in a tangible form (e.g., contained on paper or an electronic medium) for using the packaged reagents for use in a vitamin A, α-tocopherol, and a combination of β-tocopherol and γ-tocopherol quantitation assay.

Calibration and QC pools for use in embodiments of the present invention are preferably prepared using a matrix similar to the intended sample matrix, provided that the analyte(s) of interest (i.e, vitamin A, α-tocopherol, β-tocopherol, and/or γ-tocopherol) are essentially absent.

Sample Preparation for Mass Spectrometric Analysis

In preparation for mass spectrometric analysis, one or more of vitamin A, α-tocopherol, β-tocopherol, and γ-tocopherol may be enriched relative to one or more other components in the sample (e.g. protein) by various methods known in the art, including for example, liquid chromatography, filtration, centrifugation, thin layer chromatography (TLC), electrophoresis including capillary electrophoresis, affinity separations including immunoaffinity separations, extraction methods including ethyl acetate, methanol, or ethanol extraction, and the use of chaotropic agents or any combination of the above or the like.

Specifically, test samples (and in particular, biological samples such as samples comprising serum) may be subjected to liquid-liquid extraction as an initial step. Internal standard is typically added to the test samples prior to liquid-liquid extraction. In certain embodiments, the test samples are subjected to liquid-liquid extraction by mixing with equal amounts of absolute ethanol and hexanes. The relative volumes of the solvents to the volume of a test sample is easily determined by one in the art and may be about 300 microliters of test sample to about 1 ml of ethanol and 1 ml of hexanes.

Protein precipitation is another method of preparing a test sample, especially a biological test sample, such as serum. Protein purification methods are well known in the art, for example, Polson et al., *Journal of Chromatography B* 2003, 785:263-275, describes protein precipitation techniques suitable for use in methods of the present invention. Protein precipitation may be used to remove most of the protein from the sample leaving one or more of vitamin A (retinol), α-tocopherol, β-tocopherol, and γ-tocopherol in the supernatant. The samples may be centrifuged to separate the liquid supernatant from the precipitated proteins; alternatively the samples may be filtered to remove precipitated proteins. The resultant supernatant or filtrate may then be applied directly to mass spectrometry analysis; or alternatively to liquid chromatography and subsequent mass spectrometry analysis. In certain embodiments, the use of protein precipitation such as for example, formic acid protein precipitation, may obviate the need for TFLC or other on-line extraction prior to mass spectrometry or HPLC and mass spectrometry.

Another method of sample purification that may be used prior to mass spectrometry is liquid chromatography (LC). Certain methods of liquid chromatography, including HPLC, rely on relatively slow, laminar flow technology. Traditional HPLC analysis relies on column packing in which laminar flow of the sample through the column is the basis for separation of the analyte of interest from the sample. The skilled artisan will understand that separation in such columns is a partition process and may select LC, including HPLC, instruments and columns that are suitable for use with vitamin A (retinol), α-tocopherol, β-tocopherol, and γ-tocopherol. The chromatographic column typically includes a medium (i.e., a packing material) to facilitate separation of chemical moieties (i.e., fractionation). The medium may include minute particles. The particles typically include a bonded surface that interacts with the various chemical moieties to facilitate separation of the chemical moieties. One suitable bonded surface is a hydrophobic bonded surface such as an alkyl bonded or a cyano bonded surface. Alkyl bonded surfaces may include C-4, C-8, C-12, or C-18 bonded alkyl groups. In preferred embodiments, the column is a reversed phase C-12 column. The chromatographic column includes an inlet port for receiving a sample and an outlet port for discharging an effluent that includes the fractionated sample. The sample may be supplied to the inlet port directly, or from a SPE column, such as an on-line extraction column or a TFLC column.

In one embodiment, the sample may be applied to the LC column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytypic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one preferred embodiment, HPLC is conducted with a reversed phase analytical column chromatographic system. In certain preferred embodiments, a reversed phase C-12 analytical column (e.g., a Synergi Max-RP C-12 analytical column from Phenomenex Inc. (4 μm particle size, 70×3.0 mm), or equivalent) is used. In certain preferred embodiments, HPLC is performed with an isocratic flow comprising about 50% HPLC Grade methanol, about 30% acetonitrile, and about 20% dichloromethane.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, TFLC may be used for purification of vitamin A (retinol), α-tocopherol, and γ-tocopherol prior to mass spectrometry. In such embodiments, samples may be extracted using a TFLC column which captures the analyte. The analyte is then eluted and transferred on-line to an analytical HPLC column. For example, sample extraction may be accomplished with a TFLC extraction cartridge may be accomplished with a large particle size (50 μm) packed column. Sample eluted off of this column is then transferred on-line to an HPLC analytical column for further purification prior to mass spectrometry. Because the steps involved in these chromatography procedures may be linked in an automated fashion, the requirement for operator involvement during the purification of the analyte can be minimized. This feature may result in savings of time and costs, and eliminate the opportunity for operator error.

Detection and Quantitation by Mass Spectrometry

In various embodiments, vitamin A, α-tocopherol, and γ-tocopherol may be ionized by any method known to the skilled artisan. Mass spectrometry is performed using a mass spectrometer, which includes an ion source for ionizing the fractionated sample and creating charged molecules for further analysis. For example ionization of the sample may be performed by electron ionization, chemical ionization, electrospray ionization (ESI), photon ionization, atmospheric pressure chemical ionization (APCI), photoionization, atmospheric pressure photoionization (APPI), Laser diode thermal desorption (LDTD), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), and particle beam ionization. The skilled artisan will understand that the choice of ionization method may be determined based on the analyte to be measured, type of sample, the type of detector, the choice of positive versus negative mode, etc.

Vitamin A, α-tocopherol, β-tocopherol and γ-tocopherol may be ionized in positive or negative mode. In preferred embodiments, vitamin A, α-tocopherol, β-tocopherol and γ-tocopherol are ionized by APCI in positive ion mode.

In mass spectrometry techniques generally, after the sample has been ionized, the positively or negatively charged ions thereby created may be analyzed to determine a mass-to-charge ratio. Suitable analyzers for determining mass-to-charge ratios include quadrupole analyzers, ion traps analyzers, and time-of-flight analyzers. Exemplary ion trap methods are described in Bartolucci, et al., *Rapid Commun. Mass Spectrom.* 2000, 14:967-73.

The ions may be detected using several detection modes. For example, selected ions may be detected, i.e. using a selective ion monitoring mode (SIM), or alternatively, mass transitions resulting from collision induced dissociation or neutral loss may be monitored, e.g., multiple reaction monitoring (MRM) or selected reaction monitoring (SRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

Alternate modes of operating a tandem mass spectrometric instrument include product ion scanning and precursor ion scanning. For a description of these modes of operation, see, e.g., E. Michael Thurman, et al., Chromatographic-Mass Spectrometric Food Analysis for Trace Determination of Pesticide Residues, Chapter 8 (Amadeo R. Fernandez-Alba, ed., Elsevier 2005) (387).

The results of an analyte assay may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, external standards may be run with the samples, and a standard curve constructed based on ions generated from those standards. Using such a standard curve, the relative abundance of a given ion may be converted into an absolute amount of the original molecule. In certain embodiments, an internal standard is used to generate a standard curve for calculating the quantity of one or more of vitamin A (retinol), α-tocopherol, and the combination of β-tocopherol and γ-tocopherol. Methods of generating and using such standard curves are well known in the art and one of ordinary skill is capable of selecting an appropriate internal standard. For example, in preferred embodiments one or more isotopically labeled fat soluble vitamin may be used as internal standards. For example, $d_9$-α-tocopherol or $d_5$-vitamin A may be used as internal standards in the instant methods. Numerous other methods for relating the amount of an ion to the amount of the original molecule will be well known to those of ordinary skill in the art.

As used herein, an "isotopic label" produces a mass shift in the labeled molecule relative to the unlabeled molecule when analyzed by mass spectrometric techniques. Examples of suitable labels include deuterium ($^2$H), $^{13}$C, and $^{15}$N. One or more isotopic labels can be incorporated at one or more positions in the molecule and one or more kinds of isotopic labels can be used on the same isotopically labeled molecule.

One or more steps of the methods may be performed using automated machines. In certain embodiments, one or more purification steps are performed on-line, and more preferably all of the purification and mass spectrometry steps may be performed in an on-line fashion.

In certain embodiments, such as MS/MS, where precursor ions are isolated for further fragmentation, collision activated dissociation (CAD) is often used to generate fragment ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In particularly preferred embodiments, one or more of vitamin A, α-tocopherol, and γ-tocopherol in a sample are detected and/or quantified using MS/MS as follows. Samples are preferably subjected to liquid-liquid extraction, the supernatant dried and reconstituted, then subjected to liquid chromatography, preferably HPLC; the flow of liquid solvent from a chromatographic column enters the heated nebulizer interface of an MS/MS analyzer; and the solvent/analyte mixture is sprayed at a high flow rate (such as between about 0.4 and 1 ml/min) to form an aerosol cloud, which is subjected to a corona discharge. During these processes, the analyte or analytes (i.e., one or more of vitamin A, α-tocopherol, β-tocopherol and γ-tocopherol) are ionized. The ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for ions with the mass to charge ratios of precursor ions from the analyte or analytes (i.e., one or more of vitamin A, α-tocopherol, and γ-tocopherol). Precursor ions with the correct mass/charge ratios are allowed to pass into the collision chamber (Q2), while unwanted ions with any other mass/charge ratio collide with the sides of the quadrupole and are eliminated. Precursor ions entering Q2 collide with neutral argon gas molecules and fragment. The fragment ions generated are passed into quadrupole 3 (Q3), where the fragment ions of the analyte or analytes (i.e., one or more of vitamin A, α-tocopherol, β-tocopherol and γ-tocopherol) are selected while other ions are eliminated.

The methods may involve MS/MS performed in either positive or negative ion mode; preferably positive ion mode. Using standard methods well known in the art, one of ordinary skill is capable of identifying one or more fragment ions of a particular precursor ion of each analyte to be quantitated that may be used for selection in quadrupole 3 (Q3).

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC-MS methods. The areas under the peaks corresponding to particular ions, or the amplitude of such peaks, may be measured and correlated to the amount of the analyte of interest. In certain embodiments, the area under the curves, or amplitude of the peaks, for fragment ion(s) and/or precursor ions are measured to determine the amount of one or more of vitamin A, α-tocopherol, and combination of β-tocopherol and γ-tocopherol. As described above, the relative abundance of a given ion may be converted into an absolute amount of the original analyte using calibration standard curves based on peaks of one or more ions of an internal molecular standard.

The lower limits of quantitation (LLOQ) is the point where measurements become quantitatively meaningful. The analyte response at this LLOQ is identifiable, discrete and reproducible with an imprecision (i.e., relative standard deviation, or RSD) of equal to or less than 20% and an accuracy of 85% to 115%. Methods of the present invention are capable of achieving (LLOQ) for vitamin A of between about 10 mg/dL and 1.48 mg/dL, such as between about 5 mg/dL and 1.48 mg/dL, such as about 1.48 mg/dL; for α-tocopherol of between about 1.00 mg/L and 0.19 mg/L, such as between 0.50 mg/L and 0.19 mg/L, such as about 0.19 mg/L; and for combined β-tocopherol and γ-tocopherol of between about 1.00 mg/L and 0.12 mg/L, such as about 0.50 mg/L and 0.12 mg/L, such as about 0.12 mg/L.

The limit of detection (LOD) is the point at which a value is beyond the uncertainty associated with its measurement and is defined as three standard deviations from lowest measurable concentration. Methods of the present invention are capable of achieving a limit of detection (LOD) for vitamin A of between about 2.00 mcg/dL and 0.38 mcg/dL, such as between about 1.00 mcg/dL and 0.38 mcg/dL, such as about 0.38 mcg/dL; for α-tocopherol of between about 0.50 mg/L and 0.03 mg/L, such as between 0.25 mg/L and 0.03 mg/L, such as about 0.03 mg/L; and for combined β-tocopherol and γ-tocopherol of between about 0.50 mg/L and 0.03 mg/L, such as about 0.25 mg/L and 0.03 mg/L, such as about 0.03 mg/L.

The following Examples serve to illustrate the invention. These Examples are in no way intended to limit the scope of the methods.

EXAMPLES

Example 1: Sample Preparation

Standard stock solutions containing various amounts of vitamin A, stock solutions containing various amounts of α-tocopherol, and stock solutions containing various amounts of γ-tocopherol were prepared by spiking vitamin A, α-tocopherol, and γ-tocopherol in absolute ethanol. Internal standard solutions were prepared as above, but with $d_5$-retinol (i.e., $d_5$-vitamin A) and $d_9$-α-tocopherol at concentrations of about 2.5 mcg/mL and 5.0 mcg/mL, respectively. Portions of the standard stock solutions were spiked in analyte-stripped, defibrinated and delipidized serum from Biocell ("Biocell serum") for use as quality control samples (details discussed below in Example 4).

Chilled serum samples were prepared for analysis by warming to room temperature and vortexing for about 5-10 seconds. All stock standards and controls were vortexed at the same time. After vortexing, stock standards, controls, and serum samples were inspected for homogeneity. The remaining sample preparation steps were conducted with the main light in the room turned off.

Internal standard working solution was then added to all samples, along with about 1.0 ml of absolute ethanol and 1.0 ml of hexanes. The samples were then mixed for about 60-80 seconds, and centrifuged at 3000-3100 RPM (at about 4° C.) for between 5 and 8 minutes.

The resulting supernatant hexane layers were collected from each sample and transferred to a new glass tube, and evaporated to dryness under flowing nitrogen. The temperature during evaporation was about 20° C. and the evaporation was conducted under darkness. Once the solvent has been evaporated, about 1.0 mL of mobile phase (about 50% HPLC Grade methanol, about 30% acetonitrile, and about 20% dichloromethane) was added to each sample. The resulting mixtures were then vortexed for about 20-25 seconds and transferred to 96-well plates for LC-MS/MS analysis.

Example 2: Extraction of Vitamin A, α-Tocopherol, and γ-Tocopherol from Samples with Liquid Chromatography Injection of about 20 μL of sample was performed with a Cohesive Technologies Aria TLX-4 system using Aria OS V 1.5.1 or newer software.

The 20 μL sample injections were introduced into a Phenomenex Synergi Max-RP 4 μm (75×3.0 mm) analytical column. Alternatively, some samples were introduced into an Waters Atlantis T3 3 μm (50×2.1 mm) analytical column, used as a backup column. An isocratic HPLC mobile phase of about 50% HPLC Grade methanol, about 30% acetonitrile, and about 20% dichloromethane was applied to the analytical column, to separate the analytes from other species contained in the sample.

The separated analytes were then subjected to MS/MS for quantitation of vitamin A, α-tocopherol, and γ-tocopherol from each sample injection.

Example 3: Detection of Vitamin A, α-Tocopherol, and γ-Tocopherol by Tandem MS

MS/MS was performed using a Finnigan TSQ Quantum Ultra MS/MS system (Thermo Electron Corporation). The following software programs, all from Thermo Electron, were used in the Examples described herein: TSQ Ultra Quantum V 1.4.1 or newer, Xcalibur V 2.0 or newer, and LCQuan V 2.5 or newer. Liquid solvent/analyte exiting the analytical column flowed to the APCI interface of the MS/MS analyzer and ionized.

Ions passed to the first quadrupole (Q1), which selected precursor ions with a m/z of about 269.30±0.50 for vitamin A, a m/z of about 274.20±0.50 for $d_5$-retinol, a m/z of about 430.47±0.50 for α-tocopherol, and a m/z of about 416.35±0.50 for γ-tocopherol, and a m/z of about 439.50±0.50 for $d_9$-α-tocopherol. Ions entering quadrupole 2 (Q2) collided with argon gas (at a collision cell energy of between about 34 and 47 V) to generate ion fragments, which were passed to quadrupole 3 (Q3) for further selection. Mass transitions used for detection and quantitation during validation on positive polarity are listed in Table 1. The quantitation of all three analytes was accomplished simultaneously for each sample injection.

TABLE 1

Mass Transitions Monitored for Vitamin A, α-Tocopherol, and γ-Tocopherol, and Internal Standards (Positive Polarity)

| Analyte | Precursor Ion (m/z) | Product Ions (m/z) |
|---|---|---|
| Vitamin A | 269.30 ± 0.50 | 105.00 ± 0.50 |
| $d_5$-Retinol | 274.20 ± 0.50 | 93.10 ± 0.50 |
| α-Tocopherol | 430.47 ± 0.50 | 165.03 ± 0.50 |
| γ-Tocopherol | 416.35 ± 0.50 | 151.00 ± 0.50 |
| $d_9$-α-Tocopherol | 439.50 ± 0.50 | 174.10 ± 0.50 |

Several other potential precursor ions and product ions (for the above described precursor ions) were observed and could be used to supplement or replace any of the above indicated ions. Supplemental or alternate ions can be seen for Vitamin A, α-Tocopherol, and γ-Tocopherol in the exemplary spectra shown in FIGS. 1A-B, 2A-B, and 3A-B, respectively.

Example 4: Analytical Sensitivity: Lower Limit of Quantitation (LLOQ) and Limit of Detection (LOD) for Vitamin a, α-Tocopherol, and γ-Tocopherol The quantitation of vitamin A, α-tocopherol, and γ-tocopherol via monitoring the indicated transitions with a triple quadrupole tandem mass spectrometer was conducted on spiked Biocell serum samples and patient serum samples.

The LLOQ is the point where measurements become quantitatively meaningful. The analyte response at this LLOQ is identifiable, discrete and reproducible with an imprecision (i.e., relative standard deviation, or RSD) of equal to or less than 20% and an accuracy of 85% to 115%. The LLOQ was determined by assaying six levels of vitamin A, α-tocopherol, and γ-tocopherol (10 replicates for five days at each level), then determining the reproducibility.

Figure 6:
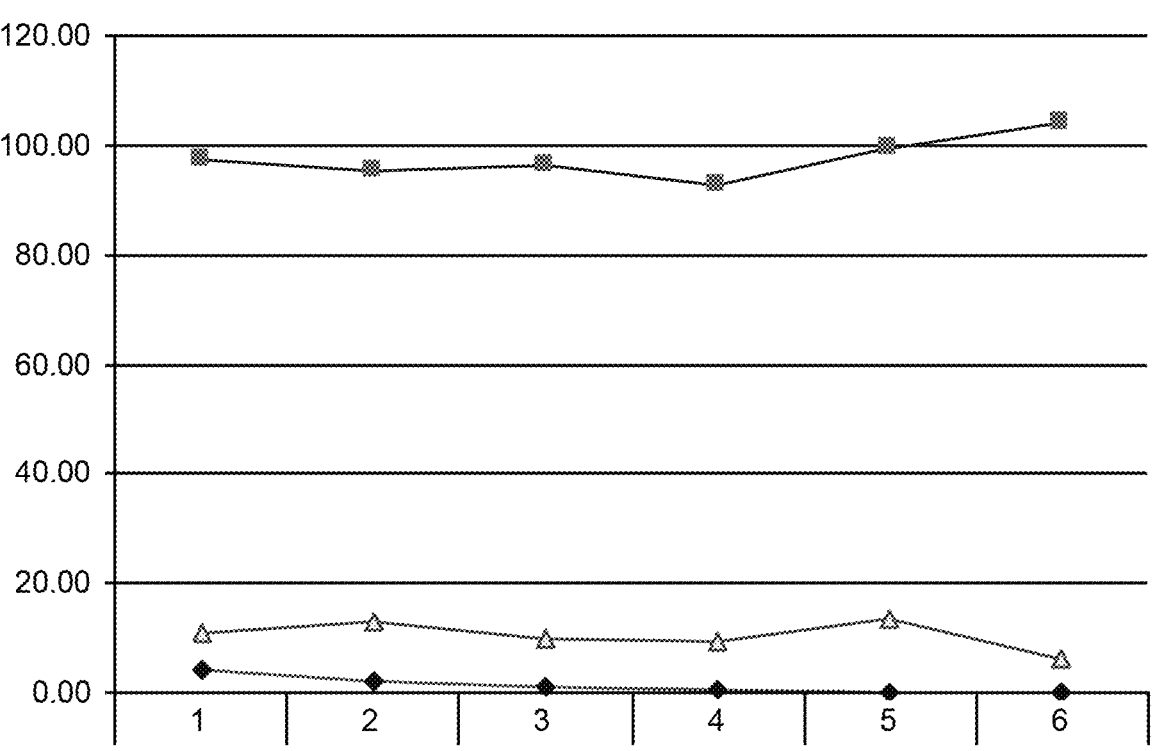
FIG. 6 shows a plot of the results from the lower linearity of quantitation studies for α-tocopherol. The data plotted with squares represent the accuracy (%); data plotted with triangles represent relative standard deviation (RSD %); and data plotted with diamonds represent concentration. Details are described in Example 4.

Analysis of data for vitamin A (shown in Table 2) shows that serum specimens in a concentration range of about 0.56 mcg/mL to about 11.8 mcg/mL yield relative standard deviations of 10.9% to 42.2% and accuracies of about 93.0% to about 158.6%. Acceptable reproducibility concentrations (RSD≤20%) are observed at 1.48 mg/dL and higher. The RSD and accuracy at low concentration levels is shown in FIG. 6.

TABLE 2

LLOQ Data for Spiked Vitamin A Serum Samples

| | Vitamin A | | | | | |
|---|---|---|---|---|---|---|
| | Standard 1 | Standard 2 | Standard 3 | Standard 4 | Standard 5 | Standard 6 |
| Actual (mcg/dL) | 0.56 | 0.74 | 1.48 | 2.95 | 5.90 | 11.80 |
| Replicate 1 | 0.56 | 0.70 | 1.56 | 3.84 | 6.45 | 11.39 |
| 2 | 1.20 | 0.45 | 1.34 | 3.51 | 6.62 | 11.47 |
| 3 | 1.00 | 0.59 | 1.49 | 3.43 | 5.37 | 13.04 |
| 4 | 0.82 | 0.61 | 1.52 | 3.35 | 6.81 | 13.13 |
| 5 | 1.16 | 0.59 | 1.74 | 3.47 | 6.29 | 9.60 |
| 6 | 0.35 | 0.98 | 1.34 | 3.27 | 6.93 | 11.85 |
| 7 | 1.28 | 0.83 | 1.34 | 3.01 | 5.11 | 10.07 |
| 8 | 0.76 | 0.58 | 1.38 | 2.99 | 5.98 | 11.04 |
| 9 | 1.06 | 0.79 | 1.41 | 3.63 | 5.80 | 12.43 |
| 10 | 0.64 | 0.91 | 1.48 | 2.78 | 5.28 | 12.73 |
| Replicate 1 | 0.59 | 0.67 | 1.20 | 3.52 | 5.18 | 10.21 |
| 2 | 0.42 | 0.71 | 1.33 | 2.74 | 4.83 | 10.50 |
| 3 | 0.61 | 0.84 | 1.60 | 2.74 | 7.40 | 11.03 |
| 4 | 1.21 | 0.42 | 1.13 | 2.61 | 5.05 | 10.39 |
| 5 | 0.56 | 0.80 | 1.32 | 2.50 | 7.13 | 9.49 |
| 6 | 0.78 | 0.34 | 1.21 | 2.60 | 6.64 | 9.29 |
| 7 | 0.56 | 0.64 | 1.28 | 3.06 | 5.94 | 11.15 |
| 8 | 1.45 | 0.85 | 1.17 | 2.57 | 6.20 | 9.89 |
| 9 | 0.99 | 0.51 | 1.01 | 2.66 | 5.10 | 11.72 |
| 10 | 1.01 | 0.82 | 1.45 | 2.98 | 5.01 | 10.77 |
| Replicate 1 | 1.48 | 0.94 | 1.55 | 2.73 | 4.65 | 12.18 |
| 2 | 1.18 | 0.99 | 1.13 | 2.40 | 4.76 | 11.54 |
| 3 | 0.60 | 1.10 | 1.49 | 3.27 | 4.58 | 12.37 |
| 4 | 0.93 | 0.83 | 1.34 | 3.11 | 3.98 | 12.85 |
| 5 | 0.71 | 0.83 | 1.47 | 2.36 | 3.85 | 12.54 |

TABLE 2-continued

LLOQ Data for Spiked Vitamin A Serum Samples

| | Vitamin A | | | | | |
| | Standard 1 | Standard 2 | Standard 3 | Standard 4 | Standard 5 | Standard 6 |
|---|---|---|---|---|---|---|
| 6 | 1.29 | 0.85 | 1.78 | 2.31 | 4.81 | 12.33 |
| 7 | 1.09 | 0.72 | 1.54 | 2.62 | 4.32 | 12.19 |
| 8 | 0.63 | 0.78 | 1.59 | 2.80 | 4.44 | 9.28 |
| 9 | 0.78 | 0.82 | 1.98 | 2.40 | 4.56 | 13.74 |
| 10 | 1.77 | 0.65 | 1.21 | 2.43 | 5.64 | 9.32 |
| Replicate 1 | 1.02 | 0.52 | 1.22 | 2.62 | 7.15 | 12.80 |
| 2 | 0.54 | 0.03 | 1.20 | 3.81 | 6.88 | 12.95 |
| 3 | 1.20 | 0.25 | 1.48 | 3.10 | 7.13 | 9.85 |
| 4 | 1.02 | 0.20 | 1.39 | 2.61 | 7.47 | 10.67 |
| 5 | 0.99 | 0.27 | 1.41 | 3.18 | 6.18 | 10.53 |
| 6 | 0.66 | 0.05 | 1.25 | 2.63 | 7.58 | 11.36 |
| 7 | 1.00 | 0.09 | 1.38 | 2.97 | 7.14 | 12.59 |
| 8 | 1.01 | 0.18 | 1.40 | 3.01 | 5.27 | 11.36 |
| 9 | 0.90 | 0.58 | 1.76 | 3.57 | 5.54 | 11.10 |
| 10 | 0.84 | 0.34 | 1.06 | 3.18 | 5.73 | 9.84 |
| Replicate 1 | 1.21 | 0.90 | 1.46 | 2.77 | 5.38 | 11.93 |
| 2 | 0.47 | 1.08 | 1.46 | 2.51 | 5.46 | 11.10 |
| 3 | 0.20 | 0.79 | 1.48 | 2.68 | 5.25 | 11.10 |
| 4 | 1.08 | 0.95 | 1.60 | 2.46 | 5.81 | 9.68 |
| 5 | 1.53 | 1.03 | 1.72 | 2.42 | 5.37 | 9.68 |
| 6 | 0.55 | 1.09 | 1.57 | 2.61 | 5.24 | 9.71 |
| 7 | 0.81 | 0.84 | 1.46 | 2.68 | 5.55 | 9.85 |
| 8 | 0.67 | 0.87 | 1.73 | 3.26 | 5.55 | 10.33 |
| 9 | 0.62 | 1.14 | 1.64 | 3.24 | 5.39 | 10.02 |
| 10 | 0.63 | 1.08 | 1.76 | 3.08 | 5.67 | 11.38 |
| Average | 0.89 | 0.69 | 1.44 | 2.92 | 5.71 | 11.15 |
| SD | 0.33 | 0.29 | 0.20 | 0.41 | 0.95 | 1.22 |
| RSD (%) | 37.3 | 42.4 | 14.3 | 14.0 | 16.7 | 10.9 |
| Accuracy (%) | 158.6 | 93.0 | 97.0 | 99.0 | 96.8 | 94.5 |

Figure 7:
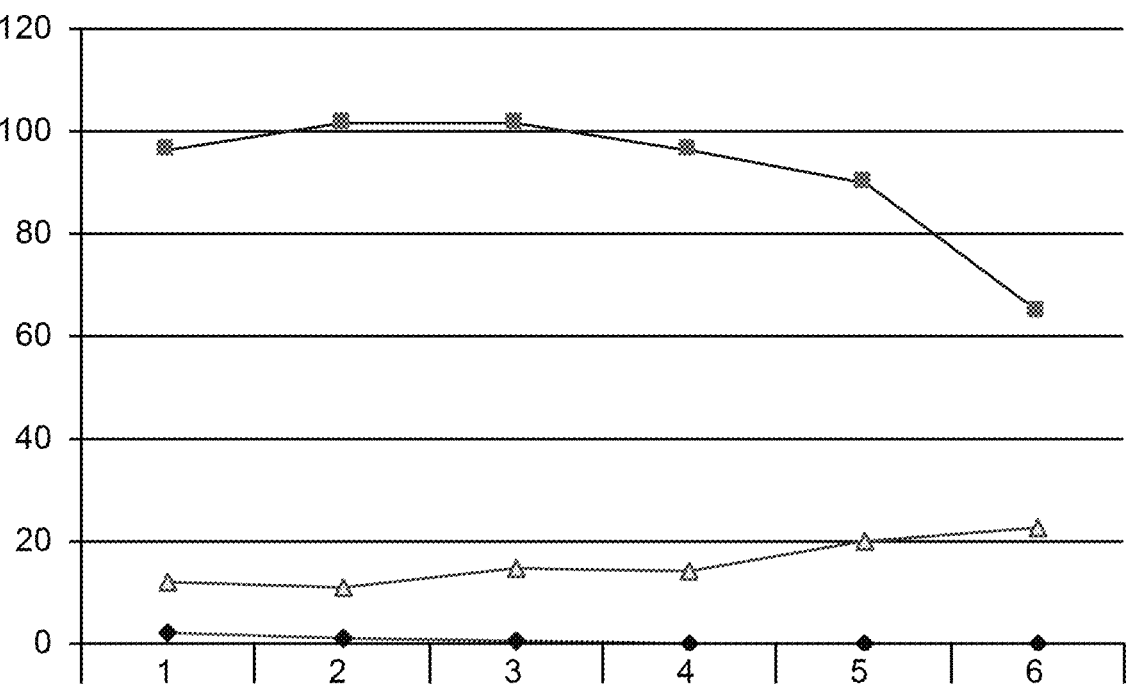
FIG. 7 shows a plot of the results from the lower linearity of quantitation studies for γ-tocopherol. The data plotted with squares represent the accuracy (%); data plotted with triangles represent relative standard deviation (RSD %); and data plotted with diamonds represent concentration. Details are described in Example 4.

Analysis of data for α-tocopherol (shown in Table 3) shows that serum specimens in a concentration range of about 0.19 mg/L to about 4.00 mg/L yield relative standard deviations of 6.3% to 13.4% and accuracies of about 92.6% to about 104.0%. Acceptable reproducibility concentrations (RSD≤20%) are observed at 0.19 mg/L and higher. The RSD and accuracy at low concentration levels is shown in FIG. 7.

TABLE 3

LLOQ Data for Spiked α-Tocopherol Serum Samples

| | α-Tocopherol | | | | | |
| | Standard 1 | Standard 2 | Standard 3 | Standard 4 | Standard 5 | Standard 6 |
|---|---|---|---|---|---|---|
| Actual (mg/L) | 0.19 | 0.25 | 0.50 | 1.00 | 2.00 | 4.00 |
| Replicate 1 | 0.18 | 0.28 | 0.48 | 1.05 | 2.15 | 4.32 |
| 2 | 0.19 | 0.26 | 0.52 | 1.10 | 2.22 | 4.36 |
| 3 | 0.19 | 0.24 | 0.48 | 1.10 | 2.18 | 4.57 |
| 4 | 0.19 | 0.26 | 0.52 | 1.18 | 2.26 | 4.51 |
| 5 | 0.20 | 0.27 | 0.53 | 1.07 | 2.32 | 4.77 |
| 6 | 0.19 | 0.25 | 0.50 | 1.07 | 2.33 | 4.22 |
| 7 | 0.19 | 0.27 | 0.57 | 1.16 | 2.09 | 4.36 |
| 8 | 0.20 | 0.28 | 0.58 | 1.15 | 2.03 | 5.55 |
| 9 | 0.19 | 0.28 | 0.54 | 1.12 | 2.18 | 4.05 |
| 10 | 0.16 | 0.28 | 0.54 | 1.18 | 2.37 | 4.19 |
| Replicate 1 | 0.20 | 0.20 | 0.44 | 0.89 | 1.94 | 4.05 |
| 2 | 0.20 | 0.23 | 0.44 | 0.93 | 2.05 | 4.10 |
| 3 | 0.21 | 0.24 | 0.42 | 0.93 | 2.17 | 3.91 |
| 4 | 0.20 | 0.25 | 0.45 | 0.88 | 2.03 | 4.20 |
| 5 | 0.22 | 0.21 | 0.47 | 0.94 | 1.98 | 3.92 |
| 6 | 0.21 | 0.25 | 0.40 | 0.96 | 2.06 | 3.95 |
| 7 | 0.20 | 0.19 | 0.41 | 0.88 | 2.12 | 4.14 |

TABLE 3-continued

LLOQ Data for Spiked α-Tocopherol Serum Samples

α-Tocopherol

|  | Standard 1 | Standard 2 | Standard 3 | Standard 4 | Standard 5 | Standard 6 |
|---|---|---|---|---|---|---|
| 8 | 0.20 | 0.24 | 0.43 | 1.02 | 2.05 | 3.88 |
| 9 | 0.19 | 0.28 | 0.46 | 1.00 | 2.07 | 4.10 |
| 10 | 0.19 | 0.21 | 0.50 | 0.96 | 2.17 | 3.80 |
| Replicate 1 | 0.21 | 0.20 | 0.44 | 0.99 | 1.91 | 3.91 |
| 2 | 0.20 | 0.19 | 0.40 | 0.95 | 1.66 | 3.56 |
| 3 | 0.21 | 0.21 | 0.39 | 1.10 | 2.11 | 3.56 |
| 4 | 0.19 | 0.21 | 0.43 | 0.92 | 1.93 | 3.54 |
| 5 | 0.19 | 0.22 | 0.42 | 0.99 | 1.86 | 3.51 |
| 6 | 0.21 | 0.20 | 0.46 | 0.95 | 1.84 | 3.61 |
| 7 | 0.20 | 0.22 | 0.47 | 0.91 | 1.93 | 3.70 |
| 8 | 0.20 | 0.20 | 0.44 | 0.94 | 1.98 | 3.78 |
| 9 | 0.19 | 0.20 | 0.40 | 1.05 | 2.07 | 3.55 |
| 10 | 0.18 | 0.19 | 0.41 | 0.96 | 2.02 | 3.72 |
| Replicate 1 | 0.18 | 0.26 | 0.45 | 0.89 | 1.60 | 3.85 |
| 2 | 0.21 | 0.25 | 0.48 | 0.82 | 1.52 | 4.17 |
| 3 | 0.22 | 0.26 | 0.50 | 0.89 | 1.51 | 3.75 |
| 4 | 0.21 | 0.28 | 0.48 | 0.86 | 1.52 | 3.74 |
| 5 | 0.21 | 0.28 | 0.44 | 0.92 | 2.20 | 3.66 |
| 6 | 0.19 | 0.24 | 0.43 | 0.86 | 1.74 | 3.87 |
| 7 | 0.18 | 0.25 | 0.47 | 0.92 | 1.62 | 3.86 |
| 8 | 0.21 | 0.24 | 0.43 | 0.88 | 1.52 | 3.63 |
| 9 | 0.19 | 0.28 | 0.43 | 0.87 | 1.51 | 3.67 |
| 10 | 0.21 | 0.23 | 0.46 | 0.91 | 1.56 | 3.98 |
| Replicate 1 | 0.20 | 0.27 | 0.49 | 0.92 | 1.69 | 3.42 |
| 2 | 0.19 | 0.28 | 0.44 | 0.90 | 1.67 | 3.61 |
| 3 | 0.20 | 0.28 | 0.45 | 0.88 | 1.78 | 3.52 |
| 4 | 0.21 | 0.27 | 0.47 | 0.88 | 1.77 | 3.47 |
| 5 | 0.20 | 0.27 | 0.47 | 0.86 | 1.68 | 3.34 |
| 6 | 0.22 | 0.30 | 0.49 | 0.90 | 1.73 | 3.64 |
| 7 | 0.21 | 0.28 | 0.46 | 0.94 | 1.74 | 3.56 |
| 8 | 0.19 | 0.27 | 0.44 | 0.91 | 1.74 | 3.65 |
| 9 | 0.20 | 0.30 | 0.48 | 0.88 | 1.66 | 3.31 |
| 10 | 0.17 | 0.31 | 0.46 | 0.87 | 1.67 | 3.40 |
| Average | 0.20 | 0.25 | 0.46 | 0.96 | 1.91 | 3.89 |
| SD | 0.01 | 0.03 | 0.04 | 0.10 | 0.25 | 0.41 |
| RSD (%) | 6.3 | 13.4 | 9.3 | 9.9 | 13.1 | 10.6 |
| Accuracy (%) | 104.0 | 99.3 | 92.6 | 96.2 | 95.5 | 97.2 |

Figure 8:
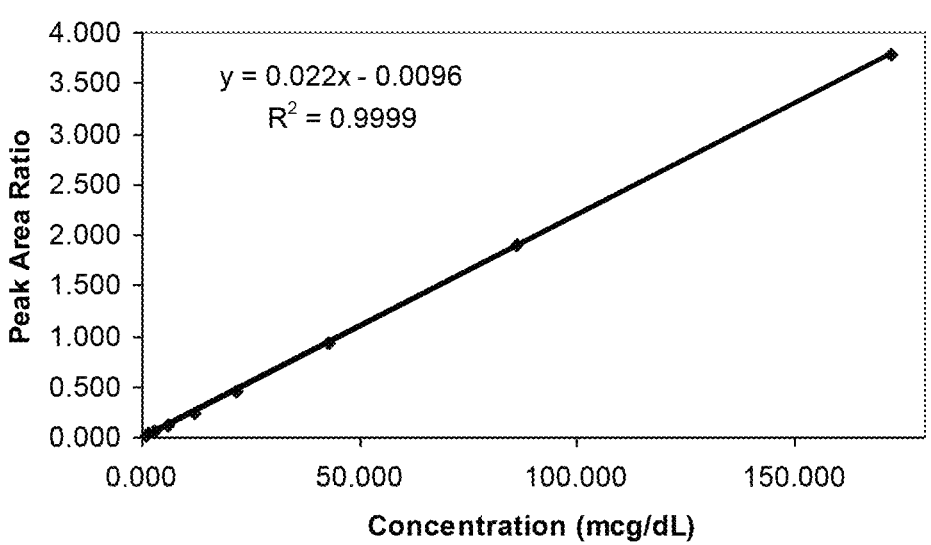
FIG. 8 shows a plot of the linearity of quantitation of vitamin A. Details are described in Example 5.

Analysis of data for γ-tocopherol spiked serum samples (shown in Table 4) shows that a concentration range of about 0.09 mg/L to about 1.95 mg/L yields relative standard deviations of 11.1% to 22.4% and accuracies of about 64.7% to about 101.3%. Acceptable reproducibility concentrations (RSD≤20%) are observed at 0.12 mg/L and higher. The RSD and accuracy at low concentration levels is shown in FIG. 8.

TABLE 4

LLOQ Data for γ-Tocopherol Spiked Serum Samples

γ-Tocopherol

|  | Standard 1 | Standard 2 | Standard 3 | Standard 4 | Standard 5 | Standard 6 |
|---|---|---|---|---|---|---|
| Actual (mg/L) | 0.09 | 0.12 | 0.24 | 0.49 | 0.98 | 1.95 |
| Replicate 1 | 0.05 | 0.13 | 0.22 | 0.48 | 0.99 | 1.84 |
| 2 | 0.08 | 0.13 | 0.24 | 0.47 | 1.05 | 1.85 |
| 3 | 0.06 | 0.11 | 0.21 | 0.50 | 0.94 | 2.01 |
| 4 | 0.05 | 0.11 | 0.22 | 0.47 | 1.02 | 1.92 |
| 5 | 0.05 | 0.11 | 0.25 | 0.47 | 1.00 | 1.92 |
| 6 | 0.08 | 0.11 | 0.23 | 0.50 | 1.01 | 1.93 |
| 7 | 0.05 | 0.12 | 0.26 | 0.51 | 1.03 | 1.72 |
| 8 | 0.07 | 0.13 | 0.26 | 0.46 | 0.91 | 2.09 |
| 9 | 0.05 | 0.13 | 0.27 | 0.55 | 0.93 | 1.94 |
| 10 | 0.04 | 0.12 | 0.26 | 0.42 | 1.05 | 2.29 |
| Replicate 1 | 0.06 | 0.09 | 0.22 | 0.39 | 0.94 | 1.82 |
| 2 | 0.05 | 0.12 | 0.18 | 0.41 | 0.90 | 1.58 |
| 3 | 0.07 | 0.13 | 0.18 | 0.38 | 1.03 | 1.65 |

TABLE 4-continued

LLOQ Data for γ-Tocopherol Spiked Serum Samples

γ-Tocopherol

|  | Standard 1 | Standard 2 | Standard 3 | Standard 4 | Standard 5 | Standard 6 |
|---|---|---|---|---|---|---|
| 4 | 0.05 | 0.14 | 0.20 | 0.41 | 0.94 | 2.06 |
| 5 | 0.04 | 0.07 | 0.22 | 0.43 | 0.95 | 1.74 |
| 6 | 0.06 | 0.07 | 0.22 | 0.44 | 1.01 | 1.82 |
| 7 | 0.07 | 0.12 | 0.21 | 0.40 | 0.84 | 1.92 |
| 8 | 0.06 | 0.13 | 0.19 | 0.46 | 0.89 | 1.67 |
| 9 | 0.05 | 0.11 | 0.18 | 0.43 | 0.89 | 1.70 |
| 10 | 0.05 | 0.11 | 0.21 | 0.43 | 0.92 | 1.66 |
| Replicate 1 | 0.06 | 0.10 | 0.20 | 0.43 | 1.03 | 1.89 |
| 2 | 0.07 | 0.07 | 0.23 | 0.57 | 1.04 | 1.71 |
| 3 | 0.06 | 0.10 | 0.22 | 0.63 | 1.19 | 1.69 |
| 4 | 0.06 | 0.06 | 0.23 | 0.54 | 1.28 | 1.78 |
| 5 | 0.06 | 0.06 | 0.22 | 0.53 | 1.10 | 1.80 |
| 6 | 0.04 | 0.10 | 0.21 | 0.53 | 1.22 | 1.95 |
| 7 | 0.05 | 0.08 | 0.28 | 0.55 | 1.28 | 2.28 |
| 8 | 0.04 | 0.09 | 0.21 | 0.54 | 1.17 | 1.77 |
| 9 | 0.07 | 0.07 | 0.29 | 0.61 | 1.13 | 2.67 |
| 10 | 0.04 | 0.07 | 0.20 | 0.60 | 1.18 | 2.50 |
| Replicate 1 | 0.07 | 0.11 | 0.26 | 0.58 | 0.92 | 2.38 |
| 2 | 0.06 | 0.12 | 0.23 | 0.50 | 0.80 | 1.97 |
| 3 | 0.06 | 0.12 | 0.29 | 0.59 | 0.87 | 1.80 |
| 4 | 0.04 | 0.12 | 0.26 | 0.59 | 1.02 | 1.82 |
| 5 | 0.05 | 0.12 | 0.30 | 0.65 | 1.08 | 1.83 |
| 6 | 0.07 | 0.12 | 0.29 | 0.60 | 0.93 | 1.78 |
| 7 | 0.04 | 0.12 | 0.28 | 0.59 | 1.03 | 1.83 |
| 8 | 0.03 | 0.11 | 0.26 | 0.58 | 0.90 | 1.79 |
| 9 | 0.06 | 0.12 | 0.21 | 0.55 | 1.08 | 1.86 |
| 10 | 0.05 | 0.12 | 0.30 | 0.57 | 0.95 | 1.86 |
| Replicate 1 | 0.06 | 0.14 | 0.23 | 0.40 | 0.92 | 1.77 |
| 2 | 0.06 | 0.13 | 0.22 | 0.53 | 0.93 | 1.87 |
| 3 | 0.06 | 0.12 | 0.22 | 0.41 | 0.89 | 1.84 |
| 4 | 0.07 | 0.11 | 0.22 | 0.45 | 0.98 | 1.72 |
| 5 | 0.05 | 0.12 | 0.24 | 0.42 | 0.88 | 1.78 |
| 6 | 0.07 | 0.08 | 0.22 | 0.49 | 0.97 | 1.93 |
| 7 | 0.08 | 0.09 | 0.24 | 0.41 | 0.88 | 1.87 |
| 8 | 0.09 | 0.13 | 0.19 | 0.43 | 0.90 | 1.94 |
| 9 | 0.08 | 0.11 | 0.18 | 0.48 | 0.93 | 1.78 |
| 10 | 0.07 | 0.09 | 0.22 | 0.47 | 0.94 | 1.39 |
| Average | 0.06 | 0.11 | 0.23 | 0.50 | 0.99 | 1.88 |
| SD | 0.01 | 0.02 | 0.03 | 0.07 | 0.11 | 0.22 |
| RSD (%) | 22.4 | 20.0 | 14.2 | 14.7 | 11.1 | 11.9 |
| Accuracy (%) | 64.7 | 89.8 | 96.5 | 101.3 | 101.3 | 96.4 |

The LOD is the point at which a value is beyond the uncertainty associated with its measurement and is defined as three standard deviations from lowest measurable concentration. To determine the LOD for vitamin A, α-tocopherol, and γ-tocopherol, ten spiked stripped serum samples at the LLOQ level were assayed, and the results analyzed. The LOD for vitamin A was determined to be 0.38 mcg/dL, while the LODs for α-tocopherol and γ-tocopherol were both determined to be 0.03 mg/L.

Figure 9:
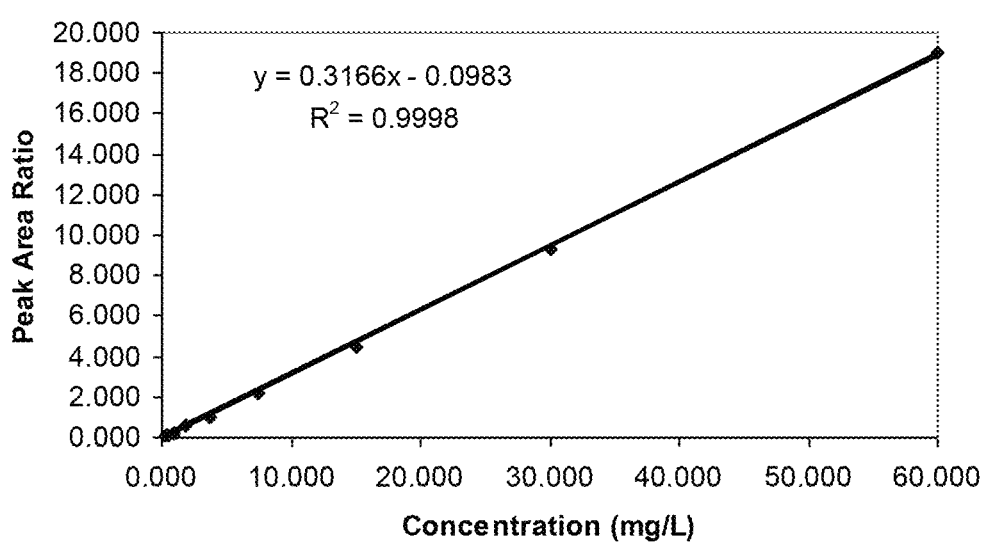
FIG. 9 shows a plot of the linearity of quantitation of α-tocopherol. Details are described in Example 5.
Figure 10:
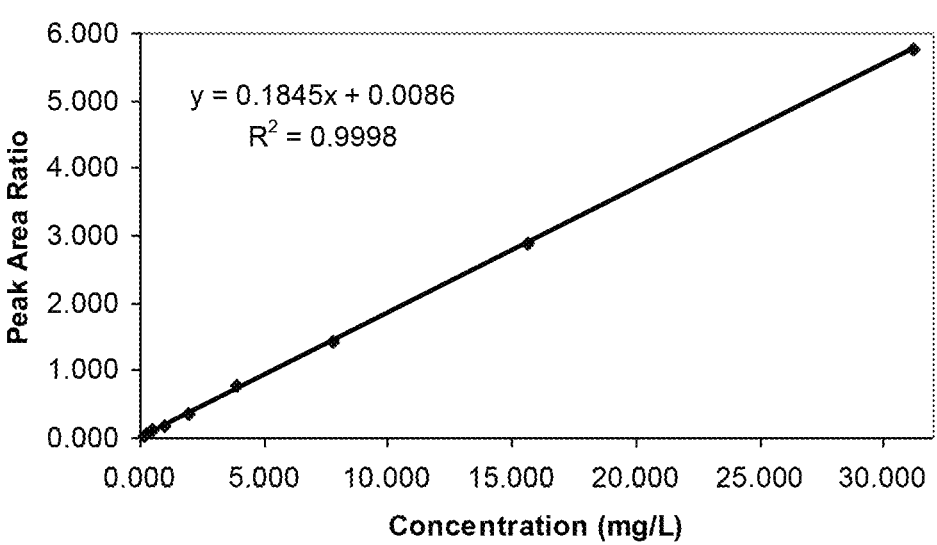
FIG. 10 shows a plot of the linearity of quantitation of β-tocopherol and/or γ-tocopherol. Details are described in Example 5.

Example 5: Linearity of Detection for Vitamin A, α-Tocopherol, and γ-Tocopherol Three separate assays, each including nine standards at various concentrations of each of vitamin A, α-tocopherol, and γ-tocopherol (ranging from about 0.74 mcg/dL to about 172.00 mcg/dL for vitamin A, about 0.24 mg/L to about 60.00 mg/L for α-tocopherol, and about 0.12 mg/L to about 31.20 mg/L for γ-tocopherol). Linear graphs were constructed using linear regression without weighting. All analytes exhibited regression coefficients ($R^2$ values) of greater than 0.9995. Plots of peak area ratios versus respective target values demonstrating the linearity of response are shown in FIGS. 9, 10, and 11 for vitamin A, α-tocopherol, and γ-tocopherol, respectively.

Example 5: Intra- and Inter-Assay Variation and Accuracy for Vitamin A, α-Tocopherol, and γ-Tocopherol Intra-assay variation is defined as the reproducibility of analysis of a sample within an assay. The RSD for the replicates of the sample at three levels were used to determine if the reproducibility is acceptable (i.e., ≤15% RSD). Twenty replicates from each of three levels were analyzed for each of the analytes (about 7.00 mcg/dL, about 30.00 mcg/dL, and about 100.00 mcg/dL for vitamin A; about 2.50 mg/L, about 10.00 mg/L, and about 22 mg/L for α-tocopherol; and about 1.50 mg/L, about 6.00 mg/L, and about 12.00 mg/L for γ-tocopherol). Data from these analyses are presented in Tables 5-7. The intra-assay variation RSDs of the three analytes were determined to be about 4.3%-6.7% for vitamin A, about 3.1%-6.1% for α-tocopherol, and about 4.1%-6.3% for γ-tocopherol.

Intra-assay accuracy is defined as the accuracy of measurement within an assay. The acceptable range of intra-assay accuracy is between 85%-115%. Twenty replicates of the three sample levels described above for each analyte were analyzed to demonstrate that the intra-assay accuracies of all three analytes are within the range of about 96.1% to about 102.9%. Results of data analysis are shown in Tables 5, 6, and 7.

TABLE 5

Intra-assay Variation Data and Results for Vitamin A

| | Vitamin A | | |
| | Low 7.00 | Medium 30.00 | High 100.00 |
| Replicate | mcg/dL | mcg/dL | mcg/dL |
|---|---|---|---|
| 1 | 7.39 | 31.25 | 104.45 |
| 2 | 7.24 | 31.20 | 100.24 |
| 3 | 6.68 | 27.28 | 103.83 |
| 4 | 6.67 | 30.12 | 102.95 |
| 5 | 6.78 | 29.41 | 93.85 |
| 6 | 7.03 | 31.45 | 105.87 |
| 7 | 7.24 | 28.00 | 105.73 |
| 8 | 7.34 | 28.05 | 105.55 |
| 9 | 7.07 | 26.33 | 102.81 |
| 10 | 6.68 | 30.66 | 109.32 |
| 11 | 6.45 | 30.32 | 106.44 |
| 12 | 7.54 | 32.23 | 105.22 |
| 13 | 6.56 | 32.16 | 101.47 |
| 14 | 6.84 | 28.61 | 105.68 |
| 15 | 7.72 | 26.60 | 108.95 |
| 16 | 7.81 | 26.74 | 96.34 |
| 17 | 6.56 | 26.86 | 99.76 |
| 18 | 7.12 | 28.24 | 94.00 |
| 19 | 6.62 | 28.00 | 105.51 |
| 20 | 6.26 | 30.48 | 99.58 |
| Mean | 6.98 | 29.20 | 102.88 |
| SD | 0.44 | 1.96 | 4.42 |
| RSD (%) | 6.3 | 6.7 | 4.3 |
| Accuracy (%) | 99.7 | 97.3 | 102.9 |

TABLE 6

Intra-assay Variation Data and Results for α-Tocopherol

| | α-Tocopherol | | |
| | Low 2.50 | Medium 10.00 | High 22.00 |
| Replicate | mg/L | mg/L | mg/L |
|---|---|---|---|
| 1 | 2.56 | 9.70 | 22.49 |
| 2 | 2.72 | 9.64 | 22.64 |
| 3 | 2.70 | 9.75 | 21.65 |
| 4 | 2.62 | 10.01 | 23.87 |
| 5 | 2.73 | 9.61 | 23.90 |
| 6 | 2.53 | 9.43 | 23.17 |
| 7 | 2.69 | 9.52 | 23.98 |
| 8 | 2.34 | 10.21 | 22.81 |
| 9 | 2.48 | 9.60 | 23.05 |
| 10 | 2.56 | 10.07 | 22.05 |
| 11 | 2.58 | 9.80 | 22.31 |
| 12 | 2.25 | 9.79 | 22.67 |
| 13 | 2.24 | 11.11 | 21.78 |
| 14 | 2.69 | 9.32 | 23.08 |
| 15 | 2.67 | 9.65 | 22.85 |
| 16 | 2.69 | 9.64 | 22.15 |
| 17 | 2.43 | 9.59 | 22.10 |
| 18 | 2.71 | 9.64 | 22.35 |
| 19 | 2.38 | 9.50 | 21.84 |
| 20 | 2.59 | 9.82 | 21.99 |
| Mean | 2.56 | 9.77 | 22.64 |
| SD | 0.16 | 0.38 | 0.71 |
| RSD (%) | 6.1 | 3.9 | 3.1 |
| Accuracy (%) | 102.3 | 97.7 | 102.9 |

TABLE 7

Intra-assay Variation Data and Results for γ-Tocopherol

| | γ-Tocopherol | | |
| | Low 1.50 | Medium 6.00 | High 12.00 |
| Replicate | mg/L | mg/L | mg/L |
|---|---|---|---|
| 1 | 1.49 | 5.62 | 11.52 |
| 2 | 1.68 | 6.04 | 11.96 |
| 3 | 1.54 | 5.44 | 11.42 |
| 4 | 1.59 | 5.50 | 12.45 |
| 5 | 1.45 | 5.68 | 12.74 |
| 6 | 1.57 | 5.69 | 12.25 |
| 7 | 1.49 | 5.77 | 12.51 |
| 8 | 1.48 | 5.77 | 11.98 |
| 9 | 1.46 | 5.92 | 12.23 |
| 10 | 1.48 | 5.66 | 12.39 |
| 11 | 1.41 | 5.97 | 12.25 |
| 12 | 1.35 | 5.46 | 10.08 |
| 13 | 1.32 | 6.40 | 12.63 |
| 14 | 1.39 | 5.89 | 12.05 |
| 15 | 1.43 | 6.11 | 11.87 |
| 16 | 1.41 | 5.74 | 12.52 |
| 17 | 1.40 | 5.65 | 12.97 |
| 18 | 1.57 | 5.52 | 12.45 |
| 19 | 1.52 | 5.86 | 11.99 |
| 20 | 1.33 | 5.68 | 12.52 |
| Mean | 1.47 | 5.77 | 12.14 |
| SD | 0.09 | 0.24 | 0.62 |
| RSD (%) | 6.3 | 4.1 | 5.1 |
| Accuracy (%) | 97.9 | 96.1 | 101.2 |

The inter-assay variation is defined as the reproducibility (RSD) of a sample between assays. The acceptable precision requirement for inter-assay study is ≤15% RSD. Ten replicates of the three sample levels described above for each analyte were analyzed on five different days. Data from these analyses are shown in Tables 8, 9, and 10. The inter-assay variation (RSD) was determined to be about 5.2%-8.1% for vitamin A, about 3.1%-6.1% for α-tocopherol, and about 4.1%-6.3% for γ-tocopherol.

Inter-assay accuracy is defined as the accuracy of measurement between assays. The acceptable range of inter-assay accuracy is between 85%-115%. The same ten replicates of the three sample levels described above for each analyte were used to demonstrate that the intra-assay accuracies of all three analytes are within the range of about 97.4% to about 104.9%. Results of data analysis are shown in Tables 8, 9, and 10.

TABLE 8

Inter-assay Variation Data and Results for Vitamin A

| | Vitamin A | | |
| | Low 7.00 | Medium 30.00 | High 100.00 |
| Replicate | mcg/dL | mcg/dL | mcg/dL |
|---|---|---|---|
| Day 1, Replicate 1 | 7.73 | 30.94 | 106.17 |
| 2 | 7.67 | 28.92 | 107.92 |
| 3 | 7.45 | 29.61 | 106.47 |
| 4 | 8.17 | 32.30 | 105.69 |
| 5 | 6.95 | 31.33 | 98.99 |
| 6 | 8.09 | 30.35 | 106.74 |
| 7 | 7.25 | 29.59 | 106.13 |
| 8 | 8.27 | 30.36 | 105.79 |
| 9 | 7.69 | 29.63 | 102.00 |
| 10 | 8.82 | 29.48 | 100.04 |
| Day 2, Replicate 1 | 7.77 | 27.37 | 109.49 |
| 2 | 7.12 | 32.10 | 95.48 |
| 3 | 7.16 | 26.80 | 102.84 |

TABLE 8-continued

Inter-assay Variation Data and Results for Vitamin A

| | Vitamin A | | |
| | Low 7.00 mcg/dL | Medium 30.00 mcg/dL | High 100.00 mcg/dL |
| Replicate | | | |
|---|---|---|---|
| 4 | 8.54 | 30.34 | 101.40 |
| 5 | 7.25 | 30.17 | 94.33 |
| 6 | 8.18 | 28.57 | 92.58 |
| 7 | 6.57 | 28.20 | 89.54 |
| 8 | 7.10 | 32.59 | 103.00 |
| 9 | 7.57 | 28.13 | 86.47 |
| 10 | 6.97 | 26.85 | 92.98 |
| Day 3, Replicate 1 | 7.29 | 31.07 | 101.74 |
| 2 | 7.72 | 33.95 | 108.52 |
| 3 | 7.76 | 29.76 | 107.71 |
| 4 | 7.56 | 31.17 | 103.01 |
| 5 | 7.95 | 32.28 | 104.53 |
| 6 | 8.17 | 33.30 | 106.64 |
| 7 | 8.32 | 27.56 | 101.57 |
| 8 | 7.64 | 27.95 | 102.68 |
| 9 | 6.73 | 28.02 | 100.84 |
| 10 | 7.49 | 29.70 | 104.00 |
| Day 4, Replicate 1 | 7.09 | 30.17 | 97.42 |
| 2 | 7.27 | 26.03 | 99.47 |
| 3 | 6.42 | 28.34 | 97.80 |
| 4 | 7.36 | 26.46 | 100.08 |
| 5 | 6.68 | 25.05 | 111.06 |
| 6 | 6.97 | 26.24 | 107.80 |
| 7 | 7.33 | 26.95 | 102.74 |
| 8 | 6.35 | 26.42 | 98.35 |
| 9 | 6.07 | 26.29 | 104.88 |
| 10 | 6.59 | 26.49 | 98.88 |
| Day 5, Replicate 1 | 7.39 | 31.25 | 104.45 |
| 2 | 7.24 | 31.20 | 100.24 |
| 3 | 6.68 | 27.28 | 103.83 |
| 4 | 6.67 | 30.12 | 102.95 |
| 5 | 6.78 | 29.41 | 93.85 |
| 6 | 7.03 | 31.45 | 105.87 |
| 7 | 7.24 | 28.00 | 105.73 |
| 8 | 7.34 | 28.06 | 105.55 |
| 9 | 7.07 | 26.33 | 102.81 |
| 10 | 6.68 | 30.66 | 109.32 |
| Mean | 7.34 | 29.21 | 102.17 |
| SD | 0.60 | 2.15 | 5.27 |
| RSD (%) | 8.1 | 7.4 | 5.2 |
| Accuracy (%) | 104.9 | 97.4 | 102.2 |

TABLE 9

Inter-assay Variation Data and Results for α-Tocopherol

| | α-Tocopherol | | |
| | Low 2.50 mg/L | Medium 10.00 mg/L | High 22.00 mg/L |
| Replicate | | | |
|---|---|---|---|
| Day 1, Replicate 1 | 2.43 | 9.72 | 22.44 |
| 2 | 2.51 | 9.39 | 22.08 |
| 3 | 2.45 | 9.74 | 22.38 |
| 4 | 2.56 | 9.24 | 22.75 |
| 5 | 2.80 | 9.80 | 22.76 |
| 6 | 2.91 | 9.58 | 22.15 |
| 7 | 2.53 | 9.50 | 22.61 |
| 8 | 2.37 | 9.53 | 22.42 |
| 9 | 2.45 | 11.03 | 22.16 |
| 10 | 2.52 | 10.77 | 22.46 |
| Day 2, Replicate 1 | 2.41 | 9.60 | 22.78 |
| 2 | 2.45 | 10.49 | 20.77 |
| 3 | 2.41 | 9.58 | 22.74 |
| 4 | 2.37 | 9.20 | 22.10 |
| 5 | 2.83 | 9.33 | 22.65 |
| 6 | 2.80 | 9.82 | 21.83 |
| 7 | 2.51 | 9.84 | 22.59 |

TABLE 9-continued

Inter-assay Variation Data and Results for α-Tocopherol

| | α-Tocopherol | | |
| | Low 2.50 mg/L | Medium 10.00 mg/L | High 22.00 mg/L |
| Replicate | | | |
|---|---|---|---|
| 8 | 2.37 | 10.52 | 21.86 |
| 9 | 2.52 | 10.61 | 19.68 |
| 10 | 2.53 | 10.59 | 20.59 |
| Day 3, Replicate 1 | 2.39 | 10.63 | 22.75 |
| 2 | 2.48 | 9.34 | 22.56 |
| 3 | 2.52 | 9.21 | 21.74 |
| 4 | 2.39 | 9.75 | 22.18 |
| 5 | 2.97 | 9.26 | 22.85 |
| 6 | 2.71 | 10.04 | 22.64 |
| 7 | 2.34 | 11.47 | 22.39 |
| 8 | 2.46 | 11.23 | 21.02 |
| 9 | 2.55 | 11.07 | 22.35 |
| 10 | 2.32 | 11.26 | 21.35 |
| Day 4, Replicate 1 | 2.13 | 9.15 | 22.31 |
| 2 | 2.17 | 8.93 | 23.19 |
| 3 | 2.20 | 9.05 | 23.48 |
| 4 | 2.15 | 8.91 | 23.42 |
| 5 | 2.09 | 9.73 | 23.47 |
| 6 | 2.13 | 9.58 | 23.32 |
| 7 | 2.03 | 9.83 | 22.09 |
| 8 | 2.06 | 9.68 | 23.33 |
| 9 | 2.32 | 9.75 | 22.36 |
| 10 | 2.06 | 9.70 | 22.49 |
| Day 5, Replicate 1 | 2.72 | 9.64 | 22.64 |
| 2 | 2.70 | 9.75 | 21.65 |
| 3 | 2.62 | 10.01 | 23.87 |
| 4 | 2.73 | 9.61 | 23.90 |
| 5 | 2.53 | 9.43 | 23.17 |
| 6 | 2.69 | 9.52 | 23.99 |
| 7 | 2.34 | 10.21 | 22.81 |
| 8 | 2.48 | 9.60 | 23.05 |
| 9 | 2.56 | 10.07 | 22.05 |
| 10 | 2.58 | 9.80 | 22.01 |
| Mean | 2.46 | 9.86 | 22.44 |
| SD | 0.22 | 0.63 | 0.83 |
| RSD (%) | 9.1 | 6.4 | 3.7 |
| Accuracy (%) | 98.5 | 98.6 | 102.0 |

TABLE 10

Inter-assay Variation Data and Results for γ-Tocopherol

| | γ-Tocopherol | | |
| | Low 1.50 mg/L | Medium 6.00 mg/L | High 12.00 mg/L |
| Replicate | | | |
|---|---|---|---|
| Day 1, Replicate 1 | 1.72 | 5.58 | 11.05 |
| 2 | 1.41 | 5.43 | 11.80 |
| 3 | 1.56 | 5.51 | 11.22 |
| 4 | 1.52 | 5.44 | 11.64 |
| 5 | 1.53 | 6.24 | 11.48 |
| 6 | 1.64 | 6.98 | 11.65 |
| 7 | 1.62 | 6.57 | 11.74 |
| 8 | 1.66 | 6.57 | 11.54 |
| 9 | 1.49 | 6.91 | 11.68 |
| 10 | 1.46 | 5.81 | 11.50 |
| Day 2, Replicate 1 | 1.51 | 5.55 | 12.71 |
| 2 | 1.41 | 5.65 | 11.51 |
| 3 | 1.48 | 5.56 | 10.99 |
| 4 | 1.49 | 5.49 | 11.39 |
| 5 | 1.45 | 5.49 | 11.57 |
| 6 | 1.59 | 6.49 | 12.55 |

TABLE 10-continued

| | γ-Tocopherol | | |
| | Low 1.50 mg/L | Medium 6.00 mg/L | High 12.00 mg/L |
| Replicate | | | |
|---|---|---|---|
| 7 | 1.58 | 6.25 | 12.40 |
| 8 | 1.53 | 6.59 | 12.68 |
| 9 | 1.53 | 6.12 | 12.38 |
| 10 | 1.54 | 6.62 | 11.82 |
| Day 3, Replicate 1 | 1.49 | 6.40 | 11.80 |
| 2 | 1.46 | 5.05 | 10.33 |
| 3 | 1.41 | 6.25 | 10.35 |
| 4 | 1.42 | 5.80 | 11.23 |
| 5 | 1.70 | 6.08 | 12.02 |
| 6 | 1.59 | 6.92 | 12.65 |
| 7 | 1.40 | 6.82 | 11.26 |
| 8 | 1.39 | 5.37 | 11.12 |
| 9 | 1.48 | 5.59 | 11.40 |
| 10 | 1.38 | 5.72 | 10.87 |
| Day 4, Replicate 1 | 1.36 | 5.38 | 12.42 |
| 2 | 1.19 | 5.51 | 13.15 |
| 3 | 1.42 | 6.04 | 12.97 |
| 4 | 1.40 | 5.56 | 12.25 |
| 5 | 1.23 | 5.63 | 11.65 |
| 6 | 1.21 | 5.71 | 12.44 |
| 7 | 1.24 | 5.67 | 11.60 |
| 8 | 1.25 | 5.97 | 11.91 |
| 9 | 1.30 | 5.56 | 11.77 |
| 10 | 1.25 | 6.05 | 11.98 |
| Day 5, Replicate 1 | 1.49 | 5.62 | 11.52 |
| 2 | 1.68 | 6.04 | 11.96 |
| 3 | 1.54 | 5.44 | 11.42 |
| 4 | 1.59 | 5.50 | 12.45 |
| 5 | 1.45 | 5.68 | 12.74 |
| 6 | 1.56 | 5.69 | 12.25 |
| 7 | 1.49 | 5.77 | 12.41 |
| 8 | 1.48 | 5.77 | 11.98 |
| 9 | 1.47 | 5.92 | 12.23 |
| 10 | 1.41 | 5.97 | 12.39 |
| Mean | 1.47 | 5.91 | 11.84 |
| SD | 0.13 | 0.47 | 0.62 |
| RSD (%) | 8.6 | 8.0 | 5.3 |
| Accuracy (%) | 97.9 | 98.4 | 98.6 |

Example 6: Matrix Specificity for Vitamin A, α-Tocopherol, and γ-Tocopherol

The effects of different matrices on the quantitation of vitamin A, α-tocopherol, and γ-tocopherol were studied with duplicate samples. One serum sample with high concentration vitamin A, α-tocopherol, and γ-tocopherol was diluted in duplicate from 2.5× to 50× with Biocell double stripped serum, deionized water, and normal saline. The study indicated that Biocell serum and normal saline could be used for dilution up to 50×. Inaccurate values for vitamin A were determined for high dilutions with deionized water.

Example 7: Recovery Studies for Vitamin A, α-Tocopherol, and γ-Tocopherol

A recovery study of spiked vitamins A, α-tocopherol, and γ-tocopherol in double stripped Biocell serum was performed in duplicates at eight different concentration levels for each analyte. All three analytes were quantitated simultaneously for each sample. Recovery was calculated using obtained values versus target values. The study yielded total recovery as 97.8%, 101.2%, and 93.4% for vitamin A, α-tocopherol, and γ-tocopherol, respectively.

Example 8: Interference Studies for Vitamin A, α-Tocopherol, and γ-Tocopherol The interference effects of other vitamins and related compounds at high concentrations, as well as the effects of drugs at concentrations of 10 mcg/mL, were studied. None of the tested vitamins and related compounds or drugs demonstrated interference effects at the concentrations tested. A listing of the compounds tested and their concentrations are shown in Tables 11 and 12.

TABLE 11

Interference of Vitamins and Related Compounds

| Analytes | Concentration (mcg/mL) | Interference |
|---|---|---|
| Vitamin K1 | 10 | No |
| Vitamin K2 | 10 | No |
| Vitamin B6 | 10 | No |
| Vitamin B12 | 10 | No |
| Folic Acid | 10 | No |
| α and β-Carotenes | 10 | No |
| Vitamin B2 | 10 | No |
| Vitamin B1 | 10 | No |
| Pyrithiamin | 10 | No |
| Folic Acid | 10 | No |
| Vitamin D2 | 800 nmol | No |
| Vitamin D3 | 800 nmol | No |

TABLE 11

Interference of Vitamins and Related Compounds

| Analytes | Concentration (mcg/mL) | Interference |
|---|---|---|
| Imipramine | 10 | No |
| Desipramine | 10 | No |
| Amitriptyline | 10 | No |
| Nortriptyline | 10 | No |
| Doxepin | 10 | No |
| N-Desmethyldoxepin | 10 | No |
| Fluoxetine | 10 | No |
| N-desmethylfluoxetine | 10 | No |
| Maprotiline | 10 | No |
| Mycophenolic Acid | 10 | No |
| Mycophenolic Acid Glucoronide | 10 | No |
| Propanolol | 10 | No |
| Clomipramine | 10 | No |
| N-Desmethylclomipramine | 10 | No |
| Felbamate | 10 | No |
| Rapamycine | 10 | No |
| Cyclosporine | 10 | No |
| Gabapentin | 10 | No |
| Zonisamide | 10 | No |
| Lidocaine | 10 | No |

Example 8: Comparison of MS/MS Method and HPLC Method for β-Tocopherol and γ-Tocopherol Results from analysis of patient samples with the above described MS/MS method were correlated to results from an HPLC method that is known to be unable to distinguish between β-tocopherol and γ-tocopherol.

The $R^2$ value from these correlation studies was 0.9742. This demonstrates that the MS/MS method described in the Examples above is also unable to distinguish between β-tocopherol and γ-tocopherol, with the resulting quantitation reflecting the combined amounts of β-tocopherol and γ-tocopherol in the samples.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

We claim:

1. A kit for a quantitative assay of simultaneously detecting vitamin A and vitamin E in a sample, the kit comprising an internal standard for analyzing vitamin A and an internal standard for analyzing vitamin E using mass spectrometry.

2. The kit of claim 1, wherein the internal standard for analyzing vitamin A is isotopically labeled vitamin A.

3. The kit of claim 2, wherein the isotopically labeled vitamin A is labeled with one or more isotopes selected from: deuterium ($^2$H), $^{13}$C, and $^{15}$N.

4. The kit of claim 3, wherein the isotopically labeled vitamin A is labeled with at least one deuterium.

5. The kit of claim 4, wherein the isotopically labeled vitamin A is d5-vitamin A.

6. The kit of claim 5, wherein the isotopically labeled vitamin A is d5-retinol.

7. The kit of claim 1, wherein the internal standard for analyzing vitamin A is present in an amount sufficient for performing at least one assay for vitamin A.

8. The kit of claim 1, wherein the internal standard for analyzing vitamin E is isotopically labeled vitamin E.

9. The kit of claim 8, wherein the isotopically labeled vitamin E is labeled with one or more isotopes selected from: deuterium ($^2$H), $^{13}$C, and $^{15}$N.

10. The kit of claim 9, wherein the isotopically labeled vitamin E is labeled with at least one deuterium.

11. The kit of claim 10, wherein the isotopically labeled vitamin E is d9-α-tocopherol.

12. The kit of claim 1, wherein the vitamin E is α-tocopherol or combined β-tocopherol and γ-tocopherol.

13. The kit of claim 1, wherein the internal standard for analyzing vitamin E is present in an amount sufficient for performing at least one assay for vitamin E.

* * * * *